US007759361B2

(12) United States Patent
Westman et al.

(10) Patent No.: US 7,759,361 B2
(45) Date of Patent: Jul. 20, 2010

(54) AZABICYCLOOCTAN-3-ONE DERIVATIVES AND USE THEREOF

(75) Inventors: Jacob Westman, Vanage (SE); Klas Wiman, Taby (SE); Galina Selivanova, Solona (SE); Vladimir Bykov, Taby (SE)

(73) Assignee: Aprea AB, Stockholm (SE)

( * ) Notice: Subject to any disclaimer, the term of this patent is extended or adjusted under 35 U.S.C. 154(b) by 72 days.

(21) Appl. No.: 10/590,054

(22) PCT Filed: Mar. 22, 2005

(86) PCT No.: PCT/SE2005/000412

§ 371 (c)(1),
(2), (4) Date: Aug. 21, 2006

(87) PCT Pub. No.: WO2005/090341

PCT Pub. Date: Sep. 29, 2005

(65) Prior Publication Data

US 2007/0142370 A1    Jun. 21, 2007

(30) Foreign Application Priority Data

Mar. 22, 2004    (SE) .................................. 0400708

(51) Int. Cl.
*A01N 43/90* (2006.01)
*C07D 453/02* (2006.01)
(52) U.S. Cl. ...................................... 514/305; 546/137
(58) Field of Classification Search ................. 546/137; 514/305
See application file for complete search history.

(56) References Cited

U.S. PATENT DOCUMENTS

| 3,726,877 | A | * | 4/1973 | Elkin et al. ................. 546/137 |
| 6,921,765 | B2 | | 7/2005 | Bykov et al. |
| 7,348,330 | B2 | | 3/2008 | Bykov et al. |
| 7,659,278 | B2 | | 2/2010 | Bykov et al. |
| 2006/0276502 | A1 | | 12/2006 | Stromblad et al. |

FOREIGN PATENT DOCUMENTS

| WO | 02/24692 A1 | 3/2002 |
| WO | 2002024692 | * 3/2002 |
| WO | 03/070250 A1 | 8/2003 |
| WO | 2004/084893 A1 | 1/2004 |

OTHER PUBLICATIONS

Freshney (Culture of Animal Cells, A Manual of Basic Technique, Alan R. Liss, Inc., 1983, New York, p. 4).*
Dermer (Bio/Technology, 1994, 12:320).*
Nielsen et al. Journal of Organic Chemistry (1966), 31(4), pp. 1053-1059.*
Singh et al. Journal of Medicinal Chemistry (1969), 12, pp. 524-526.*
Shimizu et al. Bulletin of the Chemical Society of Japan (1973), 46(5), 1520-5.*
Abstract only, accession No. 1973:499990 CAPLUS, document No. 79:99990, Dickinson et al. Univ. Missouri, Rolla, MO, USA, (1972) 118 pp. Avail.: Univ. Microfilms, Ann Arbor, Mich., Order No. 73-17,062, [ Diss. Abstr. Int. B 1973, 34(1), 116].*
Abstracts of Papers Part 2, 226th ACS National Meeting, American Chemical Society, New York, NY, Sep. 7-11, 2003.
Nahi, H. et al, "Effects of PRIMA-1 on Chronic Lymphocytic Leukemia cells with and without hemizygous p53 deletion", British Journal of Haematology, vol. 127, 2004, pp. 285-291.
Nielsen, Arnold T., "Systems with Bridgehead Nitrogen. beta-Ketols of the 1-Azabicyclo[2.2.2]octane Series", Journal of Organic Chemistry, vol. 31, Apr. 1966, pp. 1053-1059.
Okuda, Yoshinobu et al., "Regulatory role of p53 in experimental autoimmune encephalomyelitis", Journal of Neuroimmunology, vol. 135, 2003, pp. 29-37.
Rehman, Abdur et al., "Proteomic identification of heat shock protein 90 as a candidate target for p53 mutation reactivation by PRIMA-1 in breast cancer cells", Breast Cancer Research, vol. 7, No. 5, 2005, pp. R765-R774.
Sakamuri, Sukumar et al., "Synthesis of 2-alkyl-3-aryl-substituted quinuclidines as novel dopamine transporter inhibitors", Tetrahedron Letters, vol. 41, 2000, pp. 9949-9952.
Schieweck, Frank et al., "Synthesis of geminal bis(hydroxymethyl)pyrrolidine and pyrrolizidine imino sugars", J. Chem. Soc., Perkin Trans. 1, 2001, pp. 3409-3414.
Sekhar, Konjeti et al., "NADPH Oxidase Activity Is Essential for Keap1/Nrf2-mediated Induction of GCLC in Response to 2-Indol-3-yl-methylenequinuclidin-3-ols", Cancer Research, vol. 63, Sep. 1, 2003, pp. 5636-5645.
Sherr, Charles J., "Tumor surveillance via the ARF-p53 pathway", Genes & Dev., vol. 12, 1998, pp. 2984-2991.
Singh, Tara et al., "Antimalarials. Some Quinuclidine Derivatives of 7-Chloro-4-aminoquinoline and 6-Methoxy-8-aminoquinoline", Research Laboratories of Aldrich Chemical Company, vol. 12, May 1969, pp. 524-526.
Symonds, Holly et al., "p53-Dependent Apoptosis Suppresses Tumor Growth and Progression In Vivo", Cell, vol. 78, Aug. 26, 1994, pp. 703-711.
Tonder, Janne E., "Exploring the Stereoselectivity in the Peterson Reaction of Several 2-Substituted 1-Azabicyclo [2.2.2]octan-3-ones", Tetrahedron, vol. 56., 2000, pp. 1139-1146.
Vorob'Eva, et al., "Reaction of 2-Methylene-3-Oxoquinuclidine with Nucleophilic Reagents", Chemistry of Heterocyclic Compounds, vol. 10, 1977, pp. 1098-1104.
Yanina, A.D., et al., "Synthesis and pharmacological properties of 2- and 2,3-substituted quinuclidines", 1-Pharmacology, vol. 108, 1988, p. 71.
Bardeesy, Nabeel et al., "Clonal Expansion and Attenuated Apoptosis in Wilms' Tumors Ate Associated with p53 Gene Mutations", Cancer Research, vol. 55, Jan. 15, 1995, pp. 215-219.

(Continued)

*Primary Examiner*—D. Margaret Seaman
*Assistant Examiner*—Niloofar Rahmani
(74) *Attorney, Agent, or Firm*—Browdy and Neimark, PLLC

(57) ABSTRACT

Compounds of Formula (1) process for preparing them, pharmaceutical compositions comprising them. The use of compounds of formula (1) for hyperproliferative diseases, e.g. cancer as well as autoimmune diseases and heart disease.

21 Claims, 6 Drawing Sheets

OTHER PUBLICATIONS

Bennett, Martin et al., "Cell Surface Trafficking of Fas: A Rapid Mechanism of p53-Mediated Apoptosis", Science, vol. 282, Oct. 9, 1998, pp. 290-293.

Beroud et al, "p53 gene mutation: software and database", Nucleic Acids Research, vol. 26, No. 1, 1998, pp. 200-204.

Bonafe et al., "The different apoptotic potential of the p53 codon 72 alleles increases with age and modulates in vivo ischaemia-induced cell death", Cell Death and Differentiation, vol. 11, 2004, pp. 962-973.

Bondarenko et al., "Synthesis and antirrhythmic activity of derivatives of 3-aminoquinuclidine and 2-(aminomethyl) Quinuclidine", Pharmaceutical Chemistry Journal, vol. 12., 1978, pp. 1452-1455.

Bykov et al., "Mutant p53-dependent growth suppression distinguishes PRIMA-1 from known anticancer drugs: a statistcal analysis of information in the National Cancer Institute database", Carcinogenesis, vol. 23, No. 12, 2002, pp. 2011-2018.

Bykov et al., "Novel cancer therapy by reactivation of the p53 apoptosis pathway", Annals of Medicine, vol. 35, 2003, pp. 458-465.

Bykov et al., "PRIMA-1MET synergizes with cisplatin to induce tumor cell apoptosis", Oncogene, 2005, pp. 1-8.

Bykov, et al., "Reactivation of Mutant p53 and Induction of Apoptosis in Human Tumor Cells by Maleimide Analogs", The Journal of Biological Chemistry, vol. 280, No. 34, Aug. 26, 2005, pp. 30384-30391.

Bykov et al., "Restoration of the tumor suppressor function to mutant p53 by a low-molecular-weight compound", Nature Medicine, vol. 8, No. 3, Mar. 2002, pp. 282-288.

Bykov et al., "Small molecules that reactivate mutant p53", European Journal of Cancer, vol. 39, 2003, pp. 1828-1834.

Chakrabarti et al., "Rearrangement of 2-[1(3H)-Oxodihydrobenzo[c]FURAN-3-YL] Quinuclidin-3-Ones to Tetrahydrobenzo[b]Quinolizines. A novel Synthesis of Benzo[b]Quinolizine Ring Systems", Tetrahedron Letters, vol. 26, No. 35, 1985, pp. 4245-4246.

Chipuk et al., "Pharmacologic activation of p53 elicits Bax-dependent apoptosis in the absence of transcription", Cancer Cell, vol. 4, Nov. 2003, pp. 371-381.

Evan et al., "A Matter of Life and Cell Death", Science, vol. 281, Aug. 28, 1998, pp. 1317-1322.

Fisher et al., "The Fused Quinuclidine-valerolactone system", Tetrahedron, vol. 31, 1975, pp. 317-325.

Gottlieb et al., "p53 and Apoptosis", Cancer Biology, vol. 8, 1998, pp. 359-368.

Ko et al., "p53: puzzle and paradigm", Genes & Development, vol. 10, 1996, pp. 1054-1072.

Kumar et al., "Clay Catalyzed Highly Selective O-Alkylation of Primary Alcohols with Orthoesters", Tetrahedron Letters, vol. 38, No. 20, 1997, pp. 3619-3622.

Langer et al., "New Methods of Drug Delivery", Science, vol. 249, No. 4976, Sep. 28, 1990, pp. 1527-1533.

Lee et al., "Expression proteomics to p53 mutation reactivation with PRIMA-1 in breast cancer cells", Biochemical and Biophysical Research Communications, vol. 349, 2006, pp. 1117-1124.

Li et al., "Selective induction of apoptosis in mutant p53 premalignant and malignant cancer cells by PRIMA-1 through the c-Jun-NH2-kinase pathway", Mol Cancer Ther, vol. 4, No. 6, Jun. 2005, pp. 901-909.

Liang et al., "Functional p53 blocks progestin-induced VEGF expression in human breast cancer cells", Dalton cardiovascular Research Center and the Dept. of Biomedical Sciences, University of Missouri, Columbia, MO.

Lowe, III et al., "2-Aryl-azabicyclo[2.2.2]octanes as Novel Nonpeptide Substance P Antagonists", Bioorganic & Medicinal Chemistry Letters, vol. 4, No. 6, 1994, pp. 839-842.

Lowe et al., "p53 Status and the Efficacy of Cancer Therapy in Vivo", Science, New Series, vol. 266, No. 5186, Nov. 4, 1994, pp. 807-810.

Myers et al., "A New Family of Small Molecules to Probe the Reactivation of Mutant p53", J. Am. Chem. Soc., Jul. 15, 2004.

Morgan et al., "Synthesis and Cardiac Electrophysiological Activity of 2- and 3-[(Substituted phenyl)alkyl] quinuclidines. Structure-Activity Relationships", J. Med. Chem., vol. 30, 1987, pp. 2259-2269.

Mountz et al., "Defective clonal deletion and anergy induction in TCR transgenic lpr/lpr mice", Immunology, vol. 6, 1994, pp. 27-37.

Gupta et al., "Angiogenesis: a curse or cure?", Published by group.bmj.com, pp. 236-242 (Feb. 18, 2010).

Suggitt et al., "50 Years of preclinical anticancer drug screening: Empirical to target-driven approaches", Clinical Cancer Research, 11:971-981 (Feb. 1, 2005).

Satyamoorthy et al., "No longer a molecular black box - new clues to apoptosis and drug resistance in melanoma", Trends in Molecular Medicine, 7(5):191-194 (May 2001).

Non-final Office Action dated Dec. 24, 2009 in U.S. Appl. No. 10/550,516, corresponds to US 20060276502.

Final Office Action dated Aug. 18, 2009 in U.S. Appl. No. 10/550,516, corresponds to US 20060276502.

Non-final Office Action dated Jan. 9, 2009 in U.S. Appl. No. 10/550,516, corresponds to US 20060276502.

Final Office Action dated Jun. 11, 2008 in U.S. Appl. No. 10/550,516, corresponds to US 20060276502.

Non-final Office Action dated Dec. 4, 2007 in U.S. Appl. No. 10/550,516, corresponds to US 20060276502.

U.S. Appl. No. 10/505,407, now issued as U.S. Appl. No. 7,659,278, final Office Action dated Apr. 3, 2009.

Hartmann et al., "Overexpression and mutations of p53 in metastatic malignant melanomas", Int. J. Cancer, 67 (3):313-317 (Jul. 29, 1996).

* cited by examiner

AZABICYCLOOCTAN-3-ONE DERIVATIVES AND USE THEREOF

FIELD OF THE INVENTION

The present invention relates to azabicyclooctan-3-one derivatives and to the use thereof in therapy. More particularly, the present invention relates to azabicyclooctan-3-one derivatives for the treatment of disorders and diseases such as, for example cancer, autoimmune diseases and heart diseases.

BACKGROUND OF THE INVENTION

The most common target for mutations in tumors is the p53 gene. The fact that around half of all human tumors carry mutations in this gene is solid testimony as to its critical role as tumor suppressor. p53 halts the cell cycle and/or triggers apoptosis in response to various stress stimuli, including DNA damage, hypoxia, and oncogene activation (Ko and Prives, 1996; Sherr, 1998). Upon activation, p53 initiates the p53-dependent biological responses through transcriptional transactivation of specific target genes carrying p53 DNA binding motifs. In addition, the multifaceted p53 protein may promote apoptosis through repression of certain genes lacking p53 binding sites and transcription-independent mechanisms as well (Bennett et al., 1998; Gottlieb and Oren, 1998; (Ko and Prives, 1996). Analyses of a large number of mutant p53 genes in human tumors have revealed a strong selection for mutations that inactivate the specific DNA binding function of p53; most mutations in tumors are point mutations clustered in the core domain of p53 (residues 94-292) that harbours the specific DNA binding activity (Béroud and Soussi, 1998).

Both p53-induced cell cycle arrest and apoptosis could be involved in p53-mediated tumor suppression. While p53-induced cell cycle arrest could conceivably be reversed in different ways, p53-induced cell death would have advantage of being irreversible. There is indeed evidence from animal in vivo models (Symonds et al., 1994) and human tumors (Bardeesy et al., 1995) indicating that p53-dependent apoptosis plays a major role in the elimination of emerging tumors, particularly in response to oncogenic signaling. Moreover, the ability of p53 to induce apoptosis often determines the efficacy of cancer therapy (Lowe et al., 1994). Taking into account the fact that more than 50% of human tumors carry p53 mutations, it appears highly desirable to restore the function of wild type p53-mediated growth suppression to tumors. The advantage of this approach is that it will allow selective elimination of tumor cells, carrying mutant p53. Tumor cells are particularly sensitive to p53 reactivation, supposedly for two main reasons. First, tumor cells are sensitized to apoptosis due to oncogene activation (reviewed in (Evan and Littlewood, 1998)). Second, mutant p53 proteins tend to accumulate at high levels in tumor cells. Therefore, restoration of the wild type function to the abundant and presumably "activated" mutant p53 should trigger a massive apoptotic response in already sensitized tumor cells, whereas normal cells that express low or undetectable levels of p53 should not be affected. The feasibility of p53 reactivation as an anticancer strategy is supported by the fact that a wide range of mutant p53 proteins are susceptible to reactivation. A therapeutic strategy based on rescuing p53-induced apoptosis should therefore be both powerful and widely applicable.

It may be shown that malfunctioning of the p53 pathway is generally involved in a number of diseases, such as those enumerated herein above. Indeed, in addition to hyperproliferative diseases, such as cancer, various authors have shown the involvement of deficient p53 functioning in a number of other disease states, e.g. autoimmune diseases and cardiac diseases.

Thus, in an article by Mountz et al. (1994) it is stated that human autoimmune diseases share the common feature of an imbalance between the production and destruction of various cell types including lymphocytes (SLE), synovial cells (RA), and fibroblasts (scleroderma). Oncogenes, including bcl-2, p53, and myc, that regulate apoptosis are also expressed abnormally. According to the authors, specific therapies that induce apoptosis without incurring side effects should improve treatment of autoimmune disease.

Bonafe M et al. (2004) present data suggesting that p53 codon 72 polymorphism contributes to a genetically determined variability in apoptotic susceptibility among old people, which has a potentially relevant role in the context of an age-related pathologic condition, such as myocardial ischaemia.

Okuda et al. (2003) present results suggesting that p53 may be involved in the regulatory process of experimental autoimmune encephalomyelitis (EAE) through the control of cytokine production and/or the apoptotic elimination of inflammatory cells. EAE as a model for autoimmune inflammatory diseases of the central nervous system (CNS) is a widely used model for the human disease multiple sclerosis.

Taken together, these findings suggest that pharmacological restoration of p53 function would be beneficial in a number of disorders and diseases.

The present inventors have found that the compound PRIMA-1 (i.e. 2,2-bis(hydroxymethyl)-1-azabicyclo[2.2.2]octan-3-one) (disclosed in WO 02/24692), is able to induce apoptosis of cells carrying mutant p53. Later they also found some analogues to Prima-1 that showed similar results (disclosed in WO 03/070250). Nonetheless, there still remains a general need of compounds having activity in the treatment of disorders and diseases related to p53 malfunctioning. Preferably, such compounds should have improved pharmacokinetic and pharmacodynamic properties. One main objective of the present invention is to provide such compounds.

The present inventors surprisingly have found several azabicyclooctan-3-one derivatives showing high activity in the treatment of disorders and diseases related to p53 malfunctioning. They not only show high potency, but they are also believed to have very favourable ADME properties due to their higher cLogP value which will allow a high cellular uptake. Several of the analogs could also be considered as prodrugs to Prima-1.

The azabicyclooctan-3-one derivatives of the invention are considered potentially useful in the treatment of hyperproliferative diseases, autoimmune diseases and heart diseases and especially in the treatment of disorders wherein malfunctioning of the p53 pathway may be involved, and this discovery forms the basis of the present invention. Furthermore, the compounds in the present invention are believed to have additional effects that are positive for the treatment of the above mentioned disorders, such as will be further discussed herein below.

2-Substituted 3-quinuclidinones have been described earlier in biological context but not in the above-mentioned therapeutic areas. Thus, 2-[N'—(O-alkoxyphenyl)piperazinomethyl]-3-quinuclidinones (Biel et al. U.S. Pat. No. 3,598,825) have been described as nervous system depressants and amine-substituted 2-methylene 3-quinuclidinones have been described as anti-bacterial agents (Elkin et al. U.S. Pat. No. 3,726,877) and antidepressant agents (Biel et al. U.S. Pat. No. 3,462,442).

Biel et al., in U.S. Pat. No. 3,384,641, describe a method wherein 2-methylene-3-quinuclidinone is reacted with amines to form intermediates which upon heating could release the amines. The intermediates thus are used for purification of amines.

SUMMARY OF THE INVENTION

According to one aspect, the present invention relates to the use of a compound of formula (I)

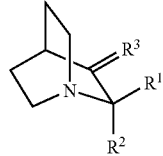

(I)

wherein (i) $R^1$ and $R^2$ are the same or different and are selected from H, $-CH_2-O-R^5$, $-CH_2-O-SO_2-R^5$, $-CH_2-S-R^5$, $-CH_2-NR^4R^5$, $-CH_2-O-CO-R^5$, $-CH_2-O-CO-NR^4R^5$ and $-CH_2-O-CO-OR^5$;

$R^3$ is $=O$, $=S$ or $=NR^5$;

$R^4$ and $R^5$ are the same or different and are selected from H; substituted or non-substituted, unbranched or branched, saturated or unsaturated C3-C12 cycloalkyl or C1-C10 alkyl; substituted or non-substituted benzyl; substituted or non-substituted mono- or bicyclic aryl; substituted or non-substituted mono-, bi- or tricyclic C1-C10 heteroaryl or non-aromatic C1-C10 heterocyclyl wherein the heteroatoms are independently selected from N, O and S; or $R^4$ and $R^5$ in $-CH_2-NR^4R^5$ are bonded together and form, together with the nitrogen atom to which they are bonded, a substituted or non-substituted non-aromatic C1-C10 mono- or bicyclic heterocyclyl optionally containing one or several further heteroatoms independently selected from N, O and S and optionally comprising one or several cyclic keto groups; with the proviso that when $R^1$ and $R^2$ are both $-CH_2-OR^5$ then $R^5$ is not H; and with the further proviso that when one of $R^1$ and $R^2$ is H and the other one is $-CH_2-NR^4R^5$, then $R^4$ and $R^5$ are not substituted or non-substituted monocyclic aryl; or (ii) $R^1$ and $R^2$ together with the carbon atom to which they are bonded form an substituted or non-substituted cyclic carbonate;

wherein the substituents of the substituted groups are selected from unbranched or branched, saturated or unsaturated C3-C12 cycloalkyl or C1-C10 allyl; halogen; mono- or bicyclic aryl; mono-, bi- or tricyclic C1-C10 heteroaryl and non-aromatic C1-C10 heterocyclyl wherein the heteroatoms are independently selected from N, O and S; C1-C10 alkyloxy; amino; C1-C10 alkylamino; $COR^6$; $CONR^6R^7$; and $COOR^6$;

$R^6$ and $R^7$ are the same or different and are selected from H; unbranched or branched, saturated or unsaturated C3-C12 cycloalkyl or C1-C10 alkyl; benzyl; mono- or bicyclic aryl; mono-, bi- or tricyclic heteroaryl or non-aromatic C1-C10 heterocyclyl wherein the heteroatoms are independently selected from N, O and S; as well as of pharmaceutically acceptable salts or prodrugs thereof, for preparing a medicament for the treatment of a disorder selected from hyperproliferative diseases, autoimmune diseases, and heart diseases.

According to a further aspect, the present invention provides the use of the compounds of formula (I) or pharmaceutically acceptable salts or prodrugs thereof for the treatment of diseases associated with mutant p53 or, more generally, a malfunctioning p53 signalling pathway.

According to another aspect, the invention provides a method of treatment of a disease selected from hyperproliferative diseases, autoimmune diseases, and heart diseases by administration of a therapeutically effective amount of a compound of formula (I) to a mammal in need of such treatment.

According to a further aspect, the invention relates to a compound of formula (I)

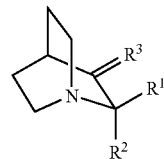

(I)

wherein (i) $R^1$ and $R^2$ are the same or different and are selected from H, $-CH_2-O-CO-R^5$, $-CH_2-O-CO-NR^4R^5$ and $-CH_2-O-CO-OR^5$;

$R^3$ is $=O$, $=S$ or $=NR^5$;

$R^4$ and $R^5$ are the same or different and are selected from H; substituted or non-substituted, unbranched or branched, saturated or unsaturated C3-C12 cycloalkyl or C1-C10 alkyl; substituted or non-substituted benzyl; substituted or non-substituted mono- or bicyclic aryl; substituted or non-substituted mono-, bi- or tricyclic C1-C10 heteroaryl or non-aromatic C1-C10 heterocyclyl wherein the heteroatoms are independently selected from N, O and S; or $R^4$ and $R^5$ in $-CH_2-NR^4R^5$ are bonded together and form, together with the nitrogen atom to which they are bonded, a substituted or non-substituted non-aromatic C1-C10 mono- or bicyclic heterocyclyl optionally containing one or several further heteroatoms independently selected from N, O and S and optionally comprising one or several cyclic keto groups; with the proviso that $R^1$ and $R^2$ are not both H; or (ii) $R^1$ and $R^2$ together with the carbon atom to which they are bonded form a substituted or non-substituted cyclic carbonate;

wherein the substituents of the substituted groups are selected from unbranched or branched, saturated or unsaturated C3-C12 cycloalkyl or C1-C10 alkyl; halogen; mono- or bicyclic aryl; mono-, bi- or tricyclic C1-C10 heteroaryl or non-aromatic C1-C10 heterocyclyl wherein the heteroatoms are independently selected from N, O and S; C1-C10 alkyloxy; amino; C1-C10 alkylamino; $COR^6$; $CONR^6R^7$; and $COOR^6$;

$R^6$ and $R^7$ are the same or different and are selected from H; unbranched or branched, saturated or unsaturated C3-C12 cycloalkyl or C1-C10 alkyl; benzyl; mono- or bicyclic aryl; mono-, bi- or tricyclic heteroaryl or non-aromatic C1-C10 heterocyclyl wherein the heteroatoms are independently selected from N, O and S; as well as pharmaceutically acceptable salts or prodrugs of the compounds of formula (I).

According to another aspect, the present invention provides methods of preparing said compounds by reacting a compound of formula (I)

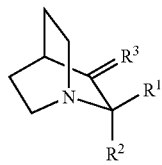

(I)

wherein R¹, R² and R³ are as defined herein above, provided that at least one of R¹ and R² is —CH₂OH; or wherein both R¹ and R² are —CH₂OH and R³ is as defined herein above; under conditions suitable for transforming at least one of R¹ and R² into —CH₂—O—CO—R⁵, —CH₂—O—CO—NR⁴R⁵ or —CH₂—O—CO—OR⁵ wherein R⁴ and R⁵ are as defined herein above.

According to a still further aspect, the invention provides new pharmaceutical compositions comprising said compounds, or salts or prodrugs thereof.

Any further aspects are as defined in the claims.

BRIEF DESCRIPTION OF THE DRAWINGS

The FIGS. 1-11 represent results from FACS analysis of a selected number of compounds.

DETAILED DESCRIPTION OF THE INVENTION

Figure 1:
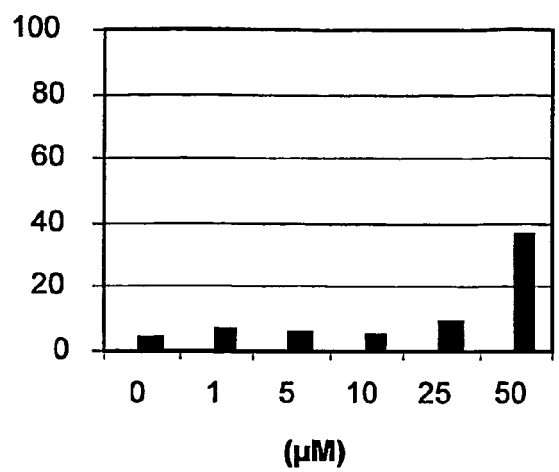
Figure 1:
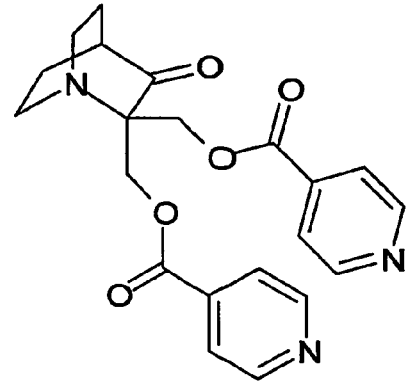
Figure 2:
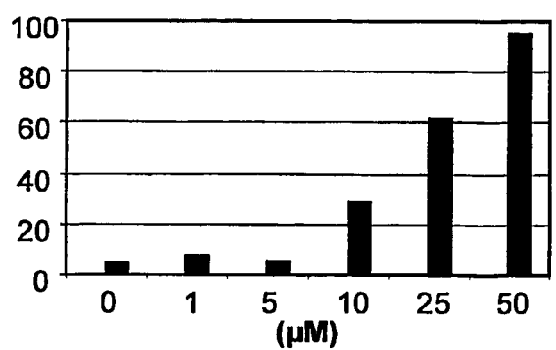
Figure 2:
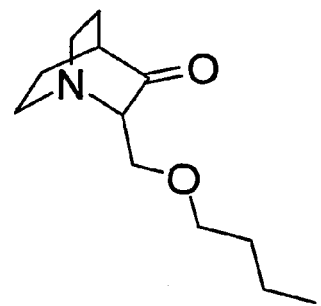
Figure 3:
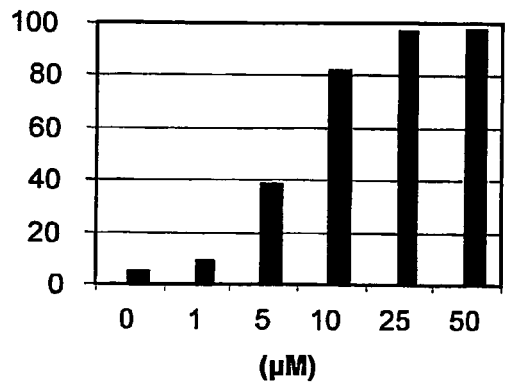
Figure 3:
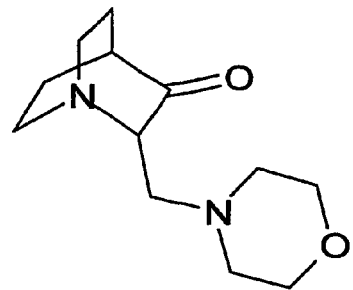
Figure 4:
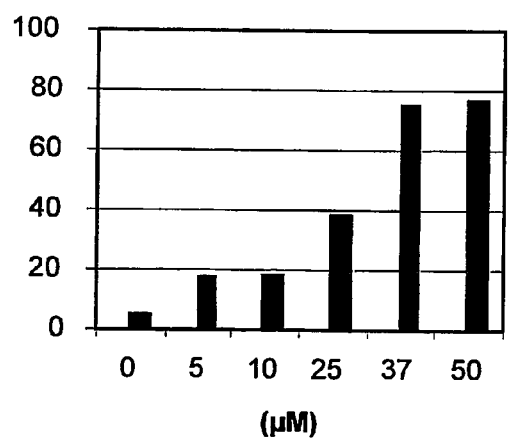
Figure 4:
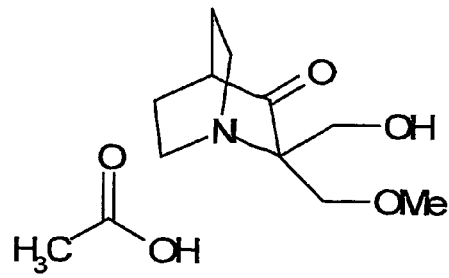
Figure 5:
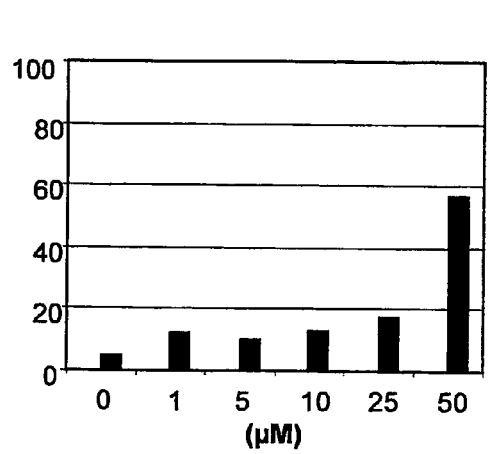
Figure 5:
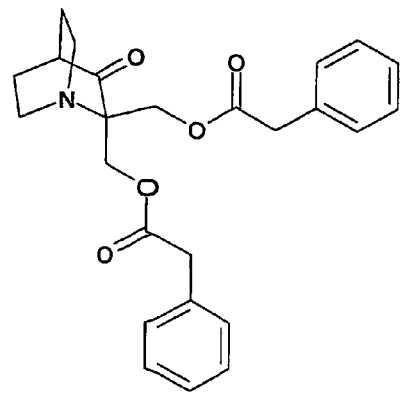
Figure 6:
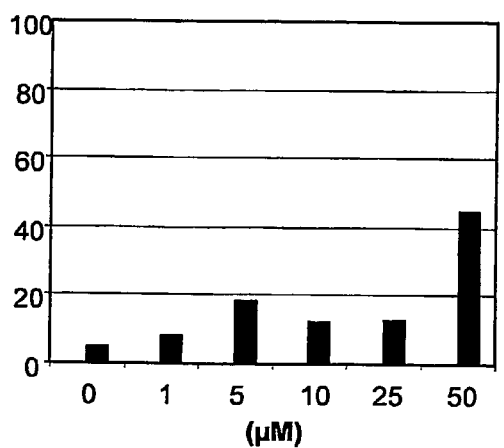
Figure 6:
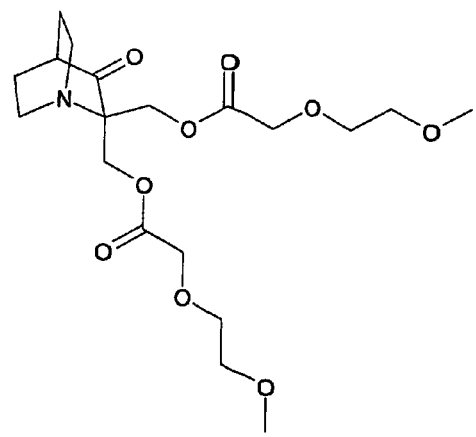
Figure 7:
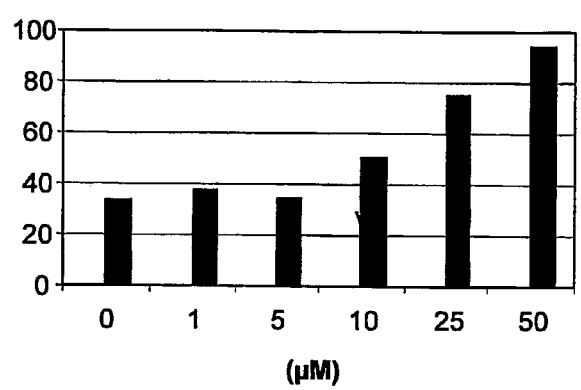
Figure 7:
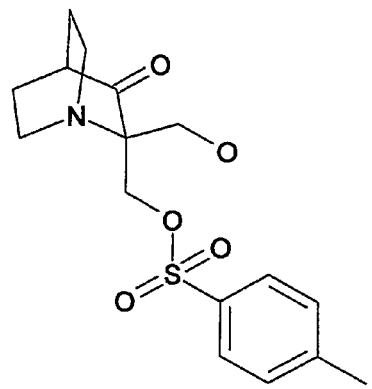
Figure 8:
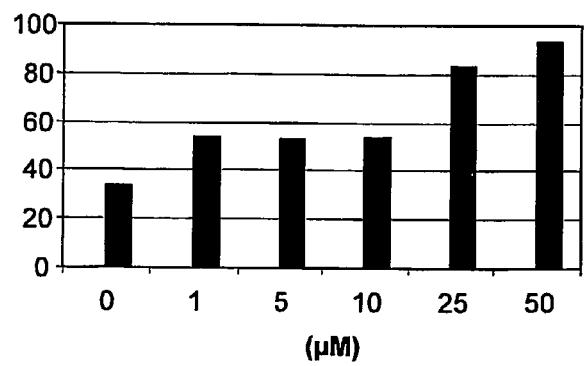
Figure 8:
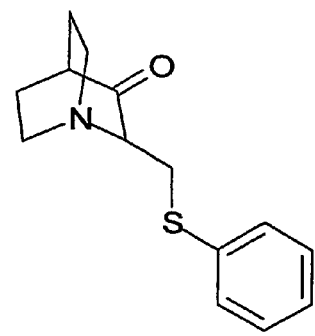
Figure 9:
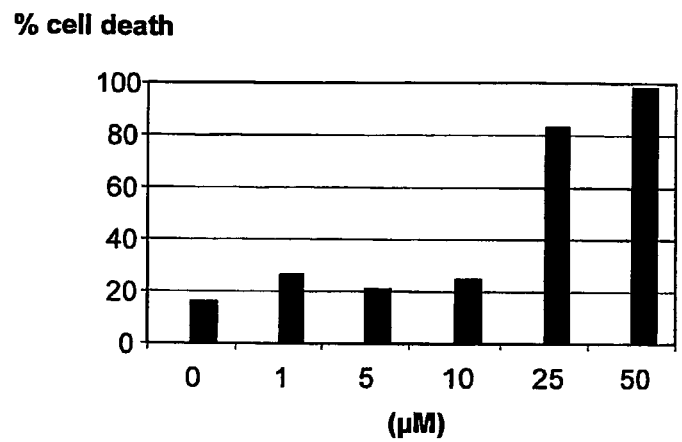
Figure 9:
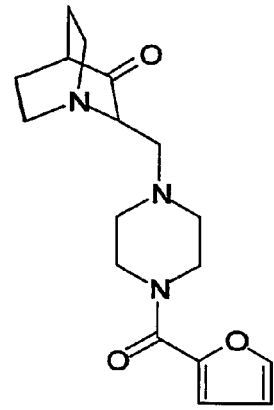
Figure 10:
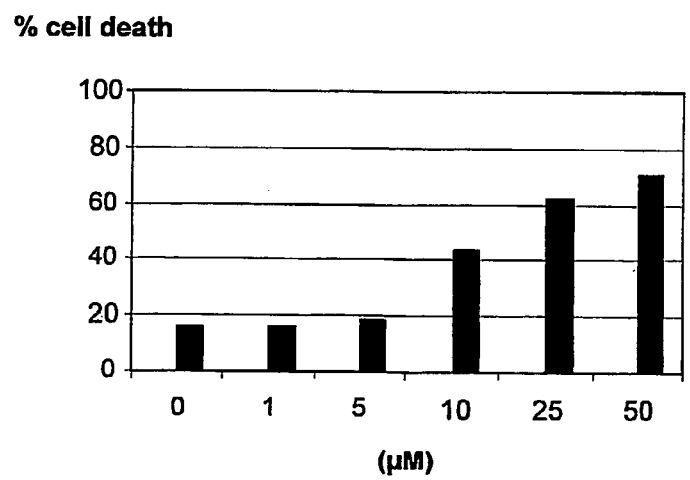
Figure 10:
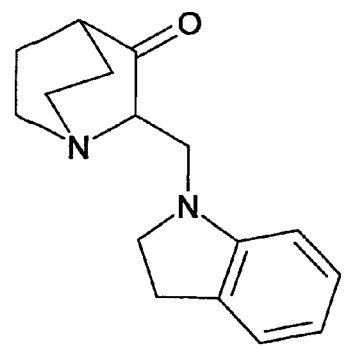
Figure 11:
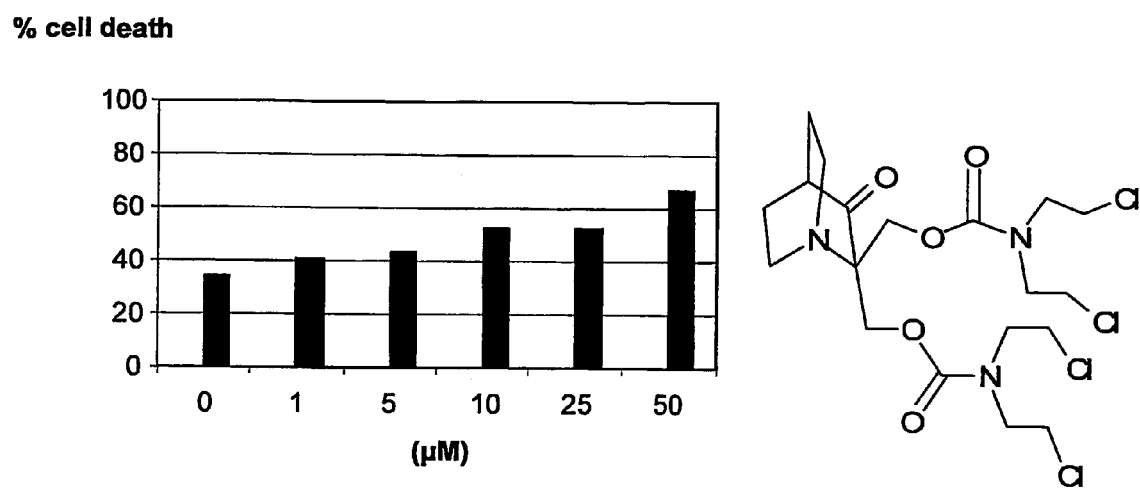

As used herein the term "lower alkyl" unless otherwise stated, means an unbranched or branched, cyclic, saturated or unsaturated (alkenyl or alkynyl) hydrocarbyl radical. Where cyclic, the alkyl group is preferably C3 to C12, more preferably C5 to C10, most preferably C5-C7. Where acyclic, the alkyl group is preferably C1 to C10, more preferably C1 to C6, more preferably methyl, ethyl, propyl (n-propyl, isopropyl), butyl (branched or unbranched) or pentyl, most preferably methyl.

As used herein, the term "aryl" means an aromatic group, such as phenyl or naphthyl. As used herein, the term "functional groups" means in the case of unprotected: hydroxy-, thiolo-, aminofunction, carboxylic acid and in the case of protected: lower alkoxy, N-, O-, S-acetyl, carboxylic acid ester.

As used herein, the term "heteroaryl" means a mono-, bi-, or tricyclic heteroaromatic group containing one or ore heteroatom(s) preferably selected from N, O and S, such as pyridyl, pyrrolyl, quinolinyl, furanyl, thienyl, oxadiazolyl, thiadiazolyl, thiazolyl, oxazolyl, pyrazolyl, triazolyl, tetrazolyl, isoxazolyl, isothiazolyl, imidazolyl, pyrimidinyl, indolyl, pyrazinyl, indazolyl, pyrimidinyl, thiophenetyl, pyranyl, carbazolyl, acridinyl, quinolinyl, benzimidazolyl, benzthiazolyl, purinyl, cinnolinyl and pteridinyl.

As used herein, the term "non-aromatic heterocycle" means a non-aromatic cyclic group containing one or more heteroatom(s) preferably selected from N, O and S, such as a pyrrolidinyl, piperidyl, piperazinyl, morpholinyl, tetrahydrofuranyl or monosaccharide.

As used herein the term "halogen" means a fluorine, chlorine, bromine or iodine.

As used herein, and unless specified otherwise, the term "substituted" means that the concerned groups are substituted with at least one functional group, such as hydroxyl, amine, sulfide, silyl, carboxylic acid, halogen, aryl, etc.

The compounds according to formula (I) will be useful for treating various diseases such as hyperproliferative diseases, e.g. cancer, autoimmune diseases, such as rheumatoid arthritis and Sjogren's syndrome, and heart diseases such as hereditary idiopatic cardiomyopathy. The treatment may be preventive, palliative or curative.

Examples of pharmaceutically acceptable addition salts for use in the pharmaceutical compositions of the present invention include those derived from mineral acids, such as hydrochlorid, hydrobromic, phosphoric, metaphosphoric, nitric and sulphuric acids, and organic acids, such as tartaric, acetic, citric, malic, lactic, fumaric, benzoic, glycolic, gluconic, succinic, and arylsulphonic acids. The pharmaceutically acceptable excipients described herein, for example, vehicles, adjuvants, carriers or diluents, are well-known to those who are skilled in the art and are readily available to the public. The pharmaceutically acceptable carrier may be one that is chemically inert to the active compounds and that has no detrimental side effects or toxicity under the conditions of use. Pharmaceutical formulations are found e.g. in Remington: The Science and Practice of Pharmacy, 19th ed., Mack Printing Company, Easton, Pa. (1995).

Prodrugs of the compounds of formula (I) may be prepared by modifying functional groups present on the compound in such a way that the modifications are cleaved, in vivo when such prodrug is administered to a mammalian subject. The modifications typically are achieved by synthesizing the parent compound with a prodrug substituent. Prodrugs include compounds of formula (I) wherein a hydroxy, amino, sulfhydryl, carboxy or carbonyl group in a compound of formula (I) is bonded to any group that may be cleaved in vivo to regenerate the free hydroxyl, amino, or sulfhydryl group, respectively. Examples of prodrugs include, but are not limited to, esters and carbamates of hydroxy functional groups, esters groups of carboxyl functional groups, N-acyl derivatives, N-Mannich bases. General information on prodrugs may be found e.g. in Bundegaard, H. "Design of Prodrugs" p 1-92, Elesevier, New York-Oxford (1985).

The composition according to the invention may be prepared for any route of administration, e.g. oral, intravenous, cutaneous or subcutaneous, nasal, intramuscular, or intraperitoneal. The precise nature of the carrier or other material will depend on the route of administration. For a parenteral administration, a parenterally acceptable aqueous solution is employed, which is pyrogen free and has requisite pH, isotonicity and stability. Those skilled in the art are well able to prepare suitable solutions and numerous methods are described in the literature. A brief review of methods of drug delivery is also found in e.g. Langer, Science 249:1527-1533 (1990).

The dose administered to a mammal, particularly a human, in the context of the present invention should be sufficient to effect a therapeutic response in the mammal over a reasonable time frame. One skilled in the art will recognize that dosage will depend upon a variety of factors including the potency of the specific compound, the age, condition and body weight of the patient, as well as the stage/severity of the disease. The dose will also be determined by the route (administration form) timing and frequency of administration. In the case of oral administration the dosage can vary from about 0.01 mg to about 1000 mg per day of a compound of formula (I) or the corresponding amount of a pharmaceutically acceptable salt thereof.

The compounds of the present invention may be used or administered in combination with one or more additional drugs useful in the treatment of hyperproleferative diseases. The components may be in the same formulation or in separate formulations for administration simultaneously or sequentially. The compounds of the present invention may also be used or administered in combination with other treatment such as irradiation for the treatment of cancer.

In their study of the inventive compounds, the present inventors found a common metabolite of many of the inventive compounds namely methylene quinuclidinone. The inventors have shown that this metabolite is able to form conjugates with gluthatione (GSH) (Reaction Scheme 1).

Reaction Scheme 1

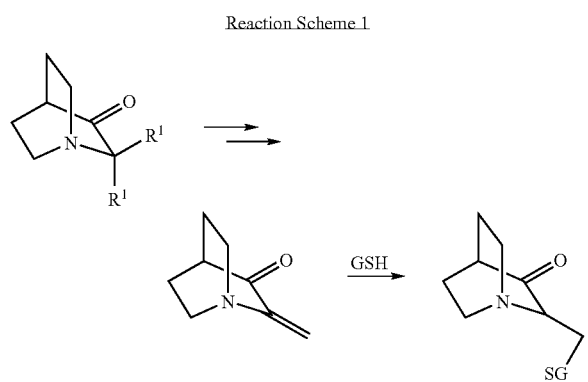

While not wishing to be bound by any theory, the inventors believe that compounds of the present invention may synergistically enhance the effect of a further pharmaceutically active compounds that in vivo are metabolized by a pathway comprising reaction with glutathione. The explanation would be that the inventive compounds, by reducing the amount of intracellular glutathione, increase the potency of the further pharmaceutically active compound. Examples of such further pharmaceutically active compounds are adriamycin, melphalan, cisplatin.

As stated herein above, according to one aspect of the invention, methods of preparing the compounds according to formula (I) are provided. Examples of synthesis of some compounds according to formula (I) are represented in the following Reaction Scheme 2:

Reaction Scheme 2

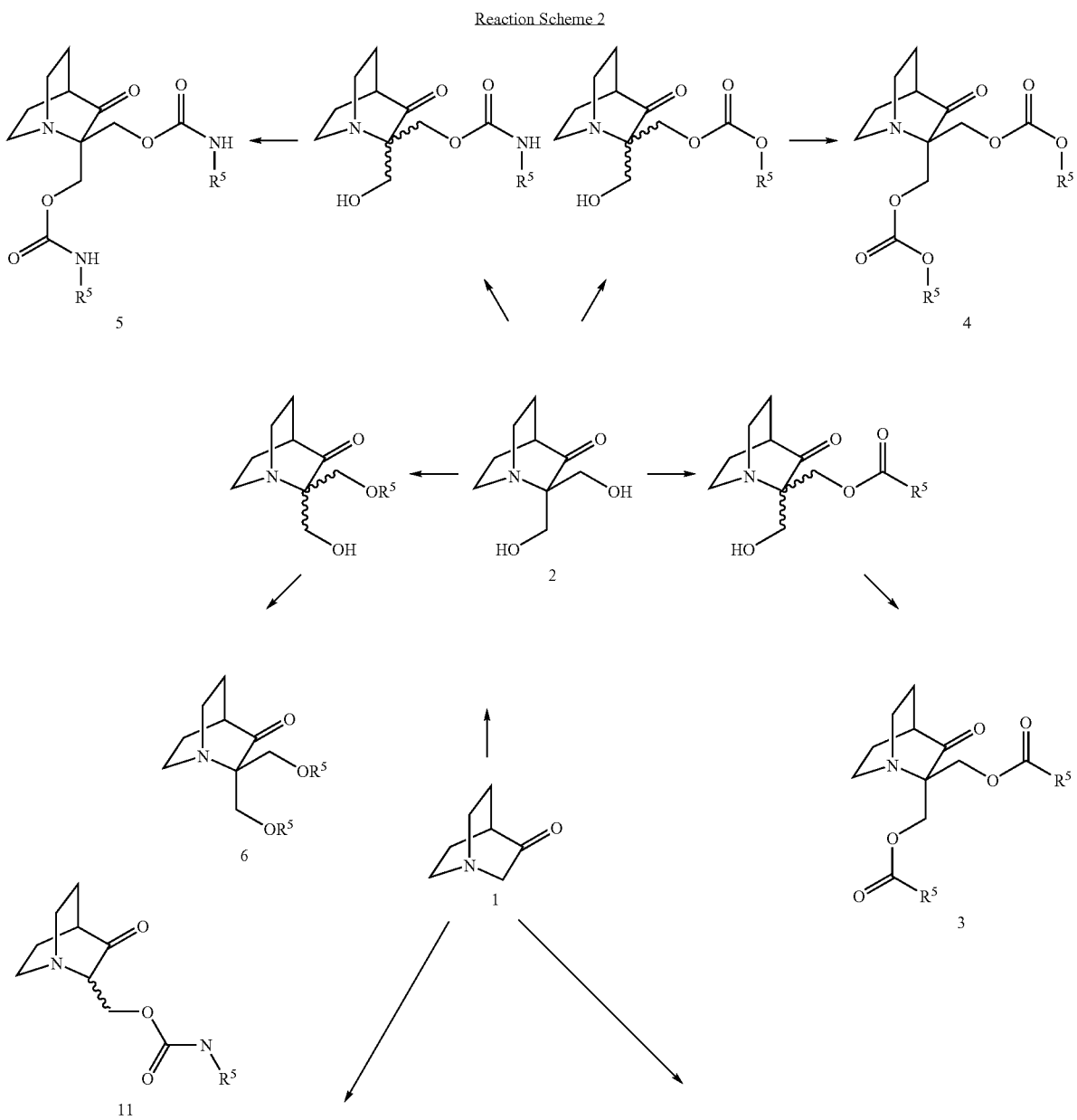

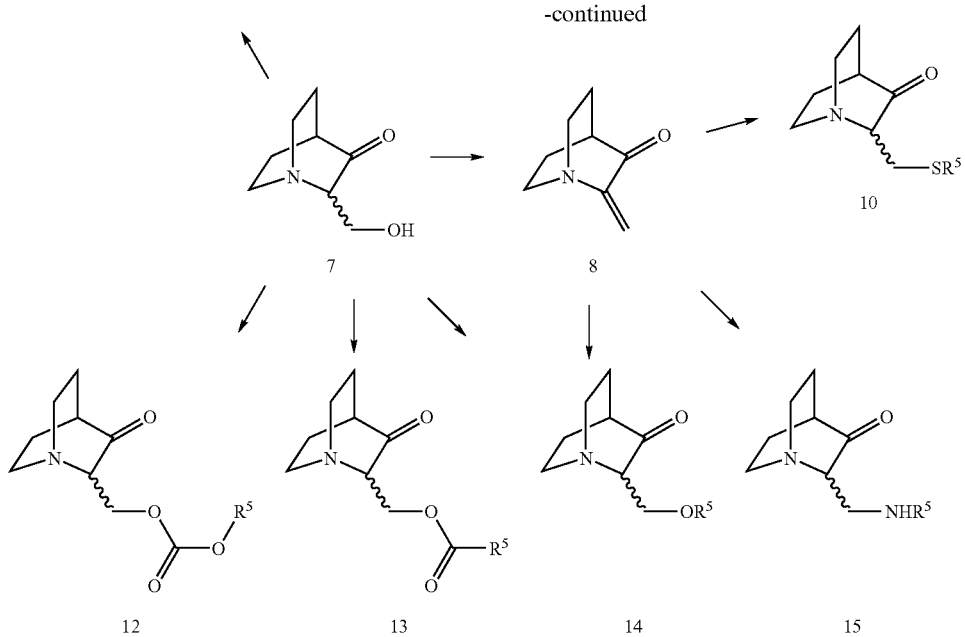

According to the Reaction Scheme 2, quinuclidinone hydrochloride (1) is used as the starting material for the synthesis of the intermediates (2), (7) and (8). 2,2-Bis-hydroxymethyl-1-aza-bicyclo[2.2.2]octan-3-one (2) is formed by treatment of (1) with an excess of formaldehyde and potassium carbonate according to methods described by Nielsen et al. (1966). 2-Hydroxymethyl-1'-aza-bicyclo[2.2.2]octan-3-one (7) is formed by treatment of quinuclidinone hydrochloride with 1 equiv. of formaldehyde and potassium carbonate. 2-Methylene-1-aza-bicyclo[2.2.2]octan-3-one (8) is formed from compound 7 by a dehydration procedure. These methods are also described by Nielsen et al. (1966); Compound 8 is also commercially available as its hydrochloride salt.

2,2-Bis-hydroxymethyl-1-aza-bicyclo[2.2.2]octan-3-one (2) forms esters by treatment with acid chlorides and a suitable base such as triethylamine, pyridine or DMAP in an organic solvent following standard protocols for acylation. The esterification may also be performed using carboxylic acids and coupling reagents such as DCC and HOBt. Carbonates and carbamates can also be formed by methods well known for the person skilled in the art. By using only 1 equiv. of the reagent the monocoupled derivatives are obtainable. The monoacylated derivative and the corresponding monocarbonate and monocarbamate may be separated from the disubstituted derivatives by liquid chromatography.

Compound 15 and analogs thereof may be formed by reaction between 2-methylene-1-aza-bicyclo[2.2.2]octan-3-one (8) and amines in organic solvents and at elevated temperature in the same way as described by Singh et al. (1969) or by Elkin et al. (U.S. Pat. No. 3,726,877).

Compound 6 and analogs thereof may be formed from 2,2-bis-hydroxymethyl-1-aza-bicyclo[2.2.2]octan-3-one (2) by alkylation, either with alkylhalides using a method as described by Schieweck et al. (2001) or by the use of orthoester as described by Sampath Kumar et al. (1997).

Compound 10 can also be formed either from compound 8 or from compound 1 by a method as described by Toender et al. (2000).

Compound 14 may be formed either by reacting compound 8 with alcohols under basic conditions as described by Nielsen et al (1966) or by alkylation of compound 7 with alkyl halides according to Schieweck et al. (2001).

The synthesis of compounds 11, 12, 13 from compound 7 may be performed by methods well known to the person skilled in the art.

EXAMPLES

Example 1

Synthesis of 2,2-Bis-hydroxymethyl-1-aza-bicyclo [2.2.2]octan-3-one (2) (intermediary)

The reaction of quinuclidinone hydrochloride (1) (commercially available) (16.9 g, 0.1 mol) with formalin (37% w/w, 150 mL, 2.0 mol) in the presence of potassium carbonate (15.9 g, 0.11 mol) consumed the starting material after 1 h at 52° C. Conversion was followed by LC-MS. The water based reaction mixture was extracted with methylene chloride (4×80 mL) and the combined organic phases were dried over MgSO$_4$. The solvent was evaporated off and heptane (500 mL) was added to the residue. After heating for one hour the hot heptane extract was discharged. Benzene (400 mL) was added to the residue followed by heating for 8 hours. The resulting mixture was clear filtered from polymer that formed during the heating, and the clear solution was evaporated to dryness. The residue was extracted with boiling heptane (300 mL).

After decanting the heptane, boiling benzene (400 mL) was added to the residue. Clear filtration and cooling (to 6° C.) followed by isolation by filtration of the solid precipitate yielded 5.1 g of 2,2-bis-hydroxymethyl-1-aza-bicyclo[2.2.2] octan-3-one (2) (mp: 136-138° C.). A second crop was isolated from combined mother liquor and material from heptane extraction after precipitation in benzene yielding 2.9 g of the product. In total 37% yield.

Example 2

Methods for O-acylation of 2,2-bis-hydroxymethyl-1-aza-bicyclo[2.2.2]octan-3-one (2)

2.1 Isobutyric acid 2-isobutyryloxymethyl-3-oxo-1-aza-bicyclo[2.2.2]oct-ylmethyl ester

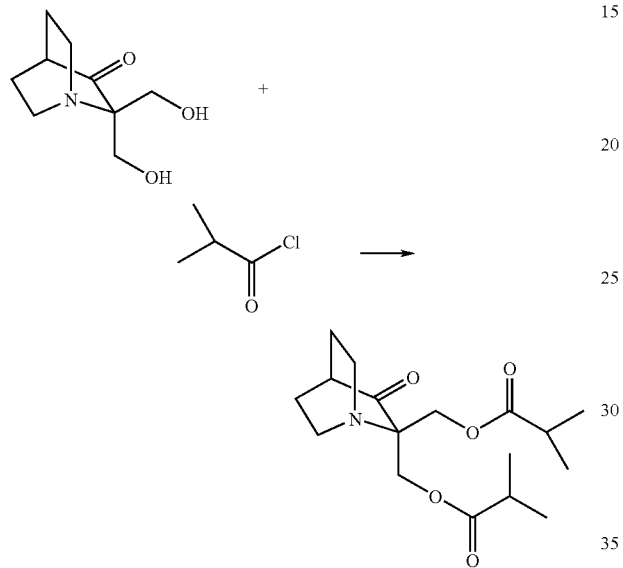

To a stirred solution of bismethylol of 3-qunuclidinone (0.25 g, 1.35 mmol) in dry dichloromethane (15 ml), 4-dimethylamino pyridine (33 mg, 0.27 mmol) and triethylamine (0.75 g, 7.4 mmol) were added under nitrogen atmosphere. The reaction mixture was cooled to 0° C., isobutyryl chloride (0.31 g, 0.9 mmol) was added slowly at 0° C. and stirring was continued for 18-20 h at room temperature (26-27° C.). The reaction mixture was quenched with cold water (25 ml), extracted with dichloromethane (3×50 ml), the organic layers were washed with 10% NaHCO₃ solution, brine and dried over sodium sulphate, filtered and concentrated to get the crude product. The crude product was purified as a viscous liquid (225 mg, 52%) by column chromatography on silica gel using 0.8:99.2 methanol:chloroform as eluent.

2.2 Acetic acid 2-acetoxymethyl-3-oxo-1-aza-bicyclo[2.2.2]oct-2-ylmethyl ester

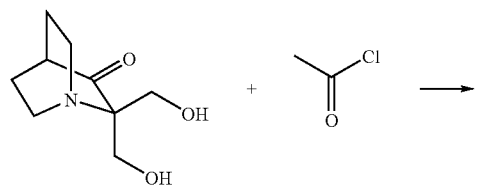

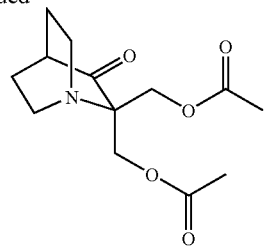

To a stirred solution of bismethylol of 3-quinuclidinone (0.25 g, 1.35 mmol) in dry dichloromethane (15 ml), 4-dimethylamino pyridine (33 mg, 0.27 mmol) and triethylamine (0.75 g, 7.4 mmol) were added under nitrogen atmosphere. The reaction mixture was cooled to 0° C., acetyl chloride (0.23 g, 2.9 mmol) was added slowly at 0° C. and stirring was continued for 18 h at room temperature (26-27° C.). The reaction mixture was quenched with cold water (25 ml), extracted with dichloromethane (3×50 ml), the organic layers were washed with 10% NaHCO₃ solution, brine and dried over sodium sulphate, filtered and concentrated to get the crude product which was purified as a yellow liquid (100 mg, 27%) by column chromatography on silica gel using 1:99 methanol:chloroform as eluent.

2.3 Dicyclobutanecarboxylic acid 3-oxo-1-aza-bicyclo[2.2.2]oct-yl-2,2 dimethyl ester

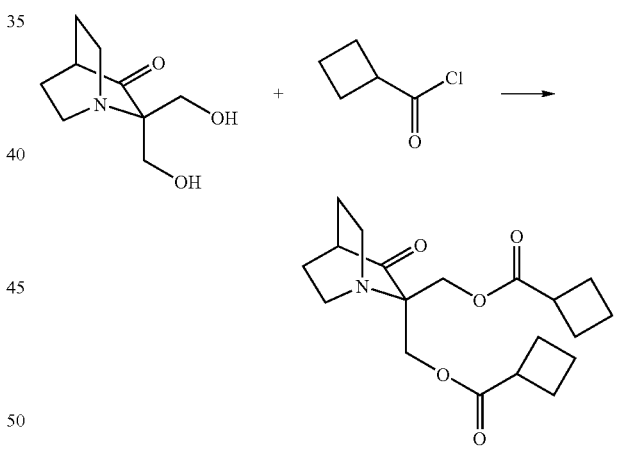

To a stirred solution of bismethylol of 3-quinuclidinone (0.25 g, 1.35 mmol) in dry dichloromethane (15 ml), 4-dimethylamino pyridine (0.41 g, 3.3 mmol) was added under nitrogen atmosphere. The reaction mixture was cooled to 0° C., cyclobutane carbonyl chloride (0.35 g, 2.9 mmol) was added slowly at 0° C. and stirring was continued for 18 h at room temperature (26-27° C.). The reaction mixture was quenched with cold water (25 ml), extracted with dichloromethane (3×50 ml), the organic layers were washed with 10% NaHCO₃ solution, brine and dried over sodium sulphate, filtered and concentrated to get the crude product which was purified as a yellow liquid (200 mg, 42.5%) by column chromatography on silica gel using 1:99 methanol:chloroform as eluent.

2.4 Dibenzoic acid 3-oxo-1-aza-bicyclo[2.2.2]oct-yl-2,2 dimethyl ester

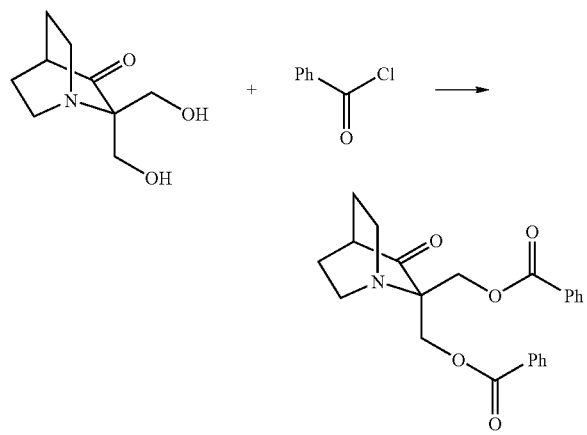

To a stirred solution of bismethylol of 3-quinuclidinone (0.25 g, 1.35 mmol) in dry dichloromethane (15 ml), 4-dimethylamino pyridine (33 mg, 0.27 mmol) and triethylamine (0.75 g, 7.4 mmol) were added under nitrogen atmosphere. The reaction mixture was cooled to 0° C., benzoyl chloride (0.41 g, 2.9 mmol) was added slowly at 0° C. and stirring was continued for 18 h at room temperature (26-27° C.). The reaction mixture was quenched with cold water (25 ml), extracted with dichloromethane (3×50 ml), the organic layers were washed with 10% NaHCO₃ solution, brine and dried over sodium sulphate, filtered and concentrated to get the crude product which was purified as off white solids (130 mg, 25%) by column chromatography on silica gel using 1:99 methanol:chloroform as eluent.

2.5 Butyric acid 2-butyryloxymethyl-3-oxo-1-aza-bicyclo[2.2.2]oct-2-ylmethyl ester

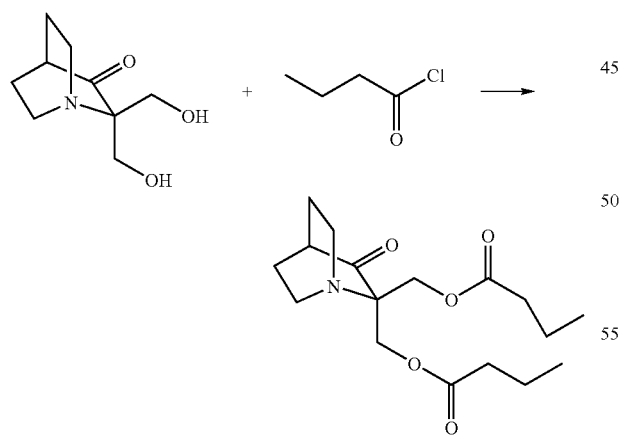

To a stirred solution of bismethylol of 3-quinuclidinone (0.25 g, 1.35 mmol) in dry dichloromethane (25 ml), 4-dimethylamino pyridine (33 mg, 0.27 mmol) and triethylamine (0.75 g, 7.4 mmol) were added under nitrogen atmosphere. The reaction mixture was cooled to –5° C., butyryl chloride (0.31 ml, 2.9 mmol) was added slowly at 0° C. and stirring was continued for 18 h at room temperature (26-27° C.). The reaction mixture was quenched with cold water (25 ml), extracted with dichloromethane (3×50 ml), the organic layers were washed with 10% NaHCO₃ solution, brine and dried over sodium sulphate, filtered and concentrated to get the crude product which was purified (316 mg, 71%) by column chromatography on silica gel using 1:99 methanol:chloroform as eluent.

2.6 Dicyclopentanecarboxylic acid 3-oxo-1-aza-bicyclo[2.2.2]oct-yl-2,2 dimethyl ester

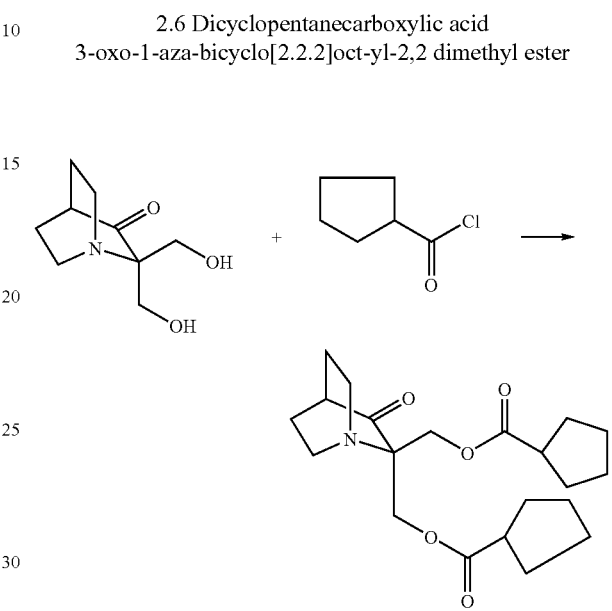

To a stirred solution of bismethylol of 3-quinuclidinone (0.25 g, 1.35 mmol) in dry dichloromethane (15 ml), 4-dimethylamino pyridine (33 mg, 0.27 mmol) and triethylamine (0.75 g, 0.0074 mol) were added under nitrogen atmosphere. The reaction mixture was cooled to 0° C., cyclopentane carbonyl chloride (0.39 g, 0.0029 mol) was added slowly at 0° C. and stirring was continued for 18 h at room temperature (26-27° C.). The reaction mixture was quenched with cold water (25 ml), extracted with dichloromethane (3×50 ml), the organic layers were washed with 10% NaHCO₃ solution, brine and dried over sodium sulphate, filtered and concentrated to get the crude product which was purified as off white solids (130 mg, 25%) by column chromatography on silica gel using 1:99 methanol:chloroform as eluent.

2.7 (2-Methoxy-ethoxy)-acetic acid 2-[2-(2-methoxy-ethoxy)-acetoxymethyl]-3-oxo-1-aza-bicyclo[2.2.2]oct-2-ylmethylester

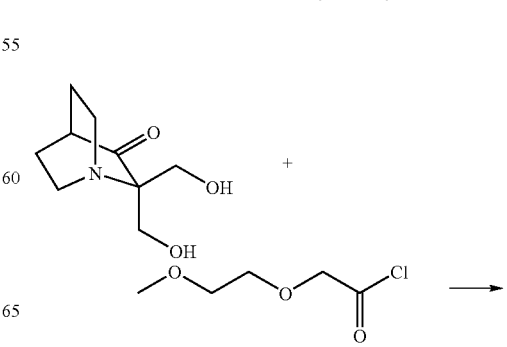

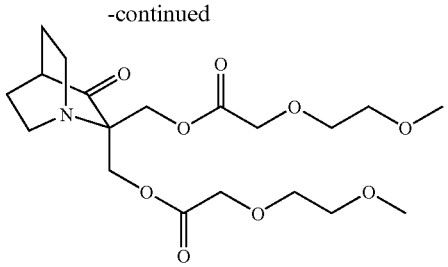

To a stirred solution of bismethylol of 3-quinuclidinone (0.25 g, 1.35 mmol) in dry dichloromethane (20 ml) triethylamine (0.75 ml) and 4-dimethylamino pyridine (33 mg) was added very slowly at −15° C. under nitrogen atmosphere. The reaction mixture was allowed to warm up to 0° C. and 2-(2-methoxy ethoxy)acetyl chloride (450 mg, 2.9 mmol) was added slowly to the reaction mixture at the same temperature under nitrogen and allowed to stir at that temperature for 1 h. Then the reaction mixture was allowed to warm up to RT and stirring was continued for overnight at RT. The completion of reaction was monitored by tlc. The reaction mixture was quenched with ice (50 g), extracted with dichloromethane (3×20 ml), organic layers were washed with 10% NaHCO₃ solution, brine and dried over sodium sulphate, filtered and concentrated to get the crude product which was purified (100 mg, 20%) by column chromatography on neutral silica gel using 99.8:0.2 chloroform:methanol as eluent.

Example 3

Methods for O-tosylation of 2,2-bis-hydroxymethyl-1-aza-bicyclo[2.2.2]octan-3-one (2)

3.1 Benzenesulfonic acid 2-hydroxymethyl-3-oxo-1-aza-bicyclo[2.2.2]oct-2-ylmethyl ester

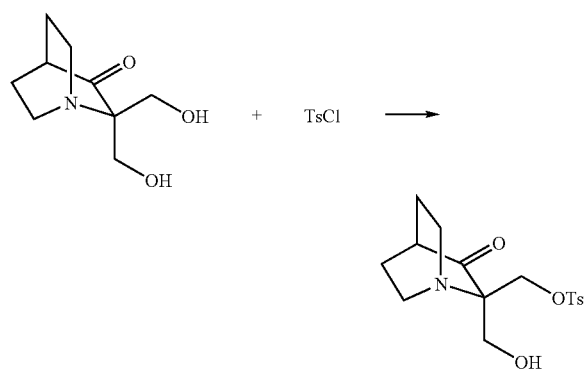

To a stirred solution of bismethylol of 3-quinuclidinone (1 g, 5.4 mmol) in dry dichloromethane (20 ml) triethylamine (1.63 g) was added very slowly at RT under nitrogen atmosphere. The reaction mixture was cooled to −20° C. and a solution of tosyl chloride (2.7 mmol) in dry dichloromethane (20 ml) was added slowly to the reaction mixture at the same temperature and allowed to stir at that temperature for 1 h. Then the reaction mixture was allowed to warm up to RT and stirring was continued for 48 h at RT. The reaction mixture was quenched with ice-cold water (50 ml), extracted with dichloromethane (3×50 ml), the organic layers were washed with brine and dried over sodium sulphate, filtered and concentrated to get the crude product which was purified (200 mg, 11%) by column chromatography on silica gel using chloroform as eluent.

Example 4

Methods for O-carboxylation of 2,2-bis-hydroxymethyl-1-aza-bicyclo[2.2.2]octan-3-one (2)

4.1 Carbonic acid 2-methoxycarbonyloxymethyl-3-oxo-1-aza-bicyclo[2.2.2]oct-2-ylmethyl ester methyl ester

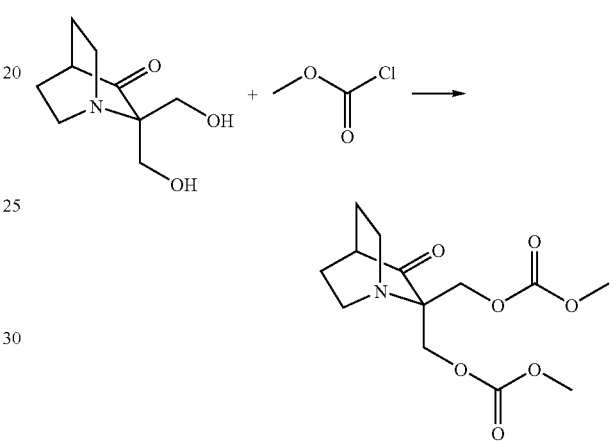

To a stirred solution of bismethylol of 3-quinuclidinone (0.5 g, 2.6 mmol) in dry dichloromethane (25 ml) pyridine (1.3 ml) was added very slowly at RT under nitrogen atmosphere. The reaction mixture was cooled to −5° C. and methyl chloroformate (0.5 ml) was added slowly to the reaction mixture at the same temperature under nitrogen and allowed to stir at that temperature for 0.5 h. Then the reaction mixture was allowed to warm up to RT and stirring was continued for 14 h at RT. The reaction mixture was quenched with ice-cold water (30 ml), extracted with dichloromethane (3×25 ml), organic layers were washed with brine and dried over sodium sulphate, filtered and concentrated to get the crude product which was purified (170 mg, 21%) by column chromatography on neutral silica gel using 98:2 chloroform:methanol as eluent.

4.2 Carbonic acid 2-isobutoxycarbonyloxymethyl-3-oxo-1-aza-bicyclo[2.2.2]oct-2-ylmethyl ester isobutyl ester

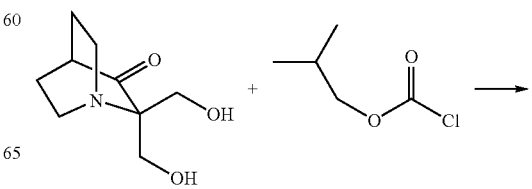

17

-continued

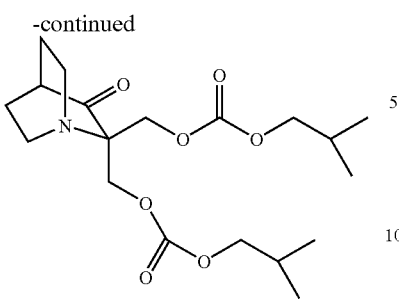

To a stirred solution of 2,2-bis-hydroxymethyl quinuclidinone (0.5 g, 2.6 mmol) in dry dichloromethane (25 ml) pyridine (1.28 g, 16.1 mmol) was added slowly at RT under nitrogen atmosphere and the reaction mixture was then cooled to 5° C. Isobutylchloroformate (0.92 g, 6.7 mmol) was added slowly to the reaction mixture at the same temperature under nitrogen and the reaction mixture was stirred for 0.5 h at the same temperature. Then the reaction mixture was allowed to warm up to RT and stirring was continued for 19 h at RT. The reaction mixture was quenched with ice-cold water (50 ml), extracted with dichloromethane (3×50 ml), washed with water, brine and dried over sodium sulphate, filtered and concentrated to get the crude product which was purified (550 mg, 55%) by column chromatography on silica gel using 0.5:99.5 methanol:chloroform as eluent.

4.3 Spiro-2,2-([1,3]-dioxan-2-one)-azabicyclo[2.2.2]octan-3-one

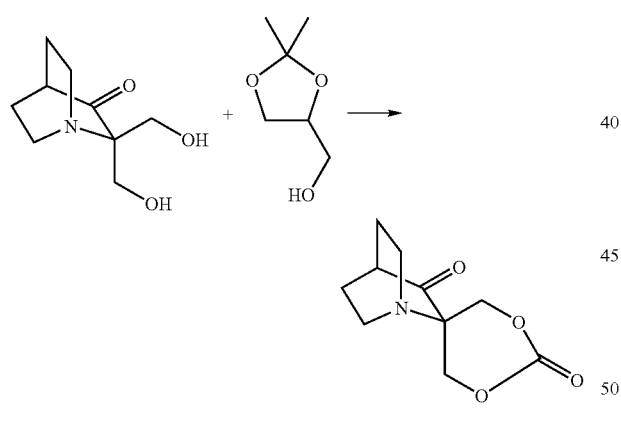

To a stirred solution of solketal (2.8 g, 0.02 mol) in dry dichloromethane (150 ml) pyridine (5 g, 0.0635 mol) was added slowly at RT under nitrogen atmosphere and the reaction mixture was then cooled to 5° C. Then a 20% solution of phosgene in toluene (15.7 ml) was added very slowly at the same temperature and stirred for 0.5 h. The reaction mixture was warmed up to RT and stirred at RT for 3 h. Again the reaction mixture was allowed to cool to 0° C. and 2.2 bis-(hydroxymethyl)quinuclidinone (1 g, 5.4 mmol) in dry dichloromethane (25 ml) was added to the reaction mixture and the reaction mixture was then warmed up to RT and stirred for 17 h at RT. The reaction mixture was quenched with ice-cold water (100 ml) and stirred for 0.5 h, extracted with dichloromethane (3×100 ml), washed with water, brine and dried over sodium sulphate, filtered and concentrated to

18 get the crude product which was purified (500 mg, 11%) by column chromatography on silica gel using 1:99 methanol:chloroform as eluent.

Example 5

Method for amination of 2-methylene-1-aza-bicyclo[2.2.2]octan-3-one (8)

5.1 5-Fluoro-1-(3-oxo-1-aza-bicyclo[2.2.2]oct-2-ylmethyl)-1H-pyrimidine-2,4-dione

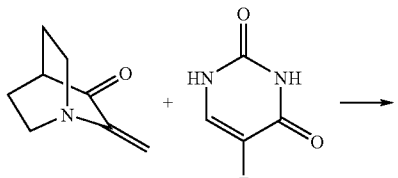

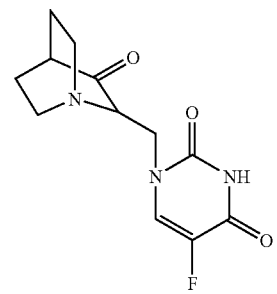

To a stirred solution of 2-methylene-3-quinuclidinone (500 mg, 3.65 mmol) in dry DMF (10 ml) 5-fluorouracil (470 mg, 3.6 mmol) was added at RT under nitrogen atmosphere. The reaction mixture was stirred at RT for 14 h. Completion of reaction was monitored by tlc. The reaction mixture was poured over crushed ice. The off-white solids that appeared were filtered and washed with hexane. The solids were then taken in chloroform and stirred for 12 h, filtered and dried to get pure product (150 mg).

5.2 2-(2,3-Dihydro-indol-1-ylmethyl)-1-aza-bicyclo[2.2.2]octan-3-one

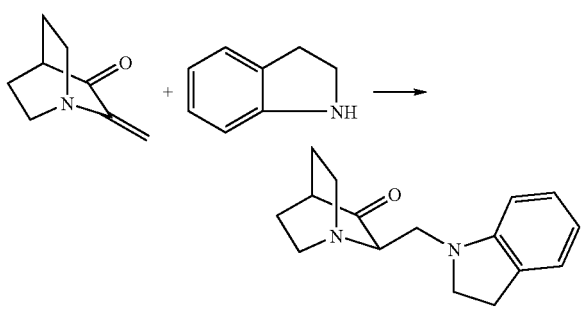

To a stirred solution of 2-methylene-3-quinuclidinone (0.5 g, 0.0028 mol) in water (6 ml) indoline (0.66 g, 0.0057 mol), triethylamine (0.84 g, 0.0084 mol) and tetra-n-butyl ammonium bromide (90 mg, 0.00028 mol) were added and the reaction mixture were allowed to stir at 80° C. for 18-20 h. The reaction mixture was quenched with ice-cold water (20 ml), extracted with dichloromethane (3×50 ml), the organic layers were washed with brine and dried over sodium sulphate, filtered and concentrated to get the crude product which was purified as greenish yellow solids (125 mg, 17%) by column chromatography on neutral silica gel using chloroform as eluent.

5.3 2-[(Ethyl-pyridin-4-ylmethyl-amino)-methyl]-1-aza-bicyclo[2.2.2]octan-3-one

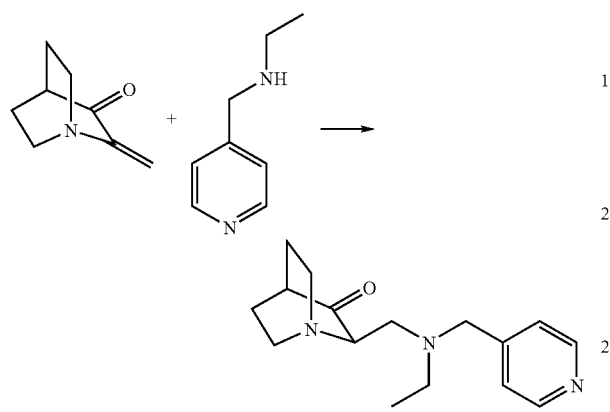

To a stirred solution of 2-methylene-3-quinuclidinone hydrochloride (0.5 g, 0.0036 mol) in water (3 ml) N-(4-pyridylmethyl)ethylamine (0.49 g, 0.0036 mol), triethylamine (1.09 g, 0.0108 mol) and tetra-n-butyl ammonium bromide (116 mg, 0.00036 mol) were added and the reaction mixture were allowed to stir at 80° C. for 18 h. The completion of reaction was monitored by tlc. The reaction mixture was quenched with ice-cold water (10 ml), extracted with dichloromethane (2×50 ml), organic layers were washed with 10% NaHCO$_3$ solution, brine and dried over sodium sulphate, filtered and concentrated to get the crude product which was purified as yellow solids (200 mg, 22%) by flash column chromatography on neutral silica gel using chloroform as eluent.

5.4 2-[4-(Furan-2-carbonyl)-piperazin-1-ylmethyl]-1-aza-bicyclo[2.2.2]octan-3-one

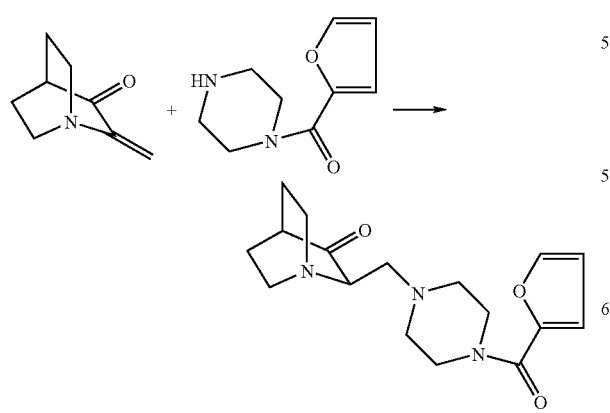

To a stirred solution of 2-methylene-3-quinuclidinone hydrochloride (0.5 g, 0.0036 mol) in water (3 ml) 1-(2-furoyl) piperazine (0.64 g, 0.0036 mol), triethylamine (1.09 g, 0.0108 mol) and tetra-n-butyl ammonium bromide (116 mg, 0.00036 mol) were added and the reaction mixture was allowed to stir at 80° C. for 20 h. The completion of reaction was monitored by tlc. The reaction mixture was quenched with ice-cold water (10 ml), extracted with dichloromethane (2×50 ml), the organic layers were washed with 10% NaHCO$_3$ solution, brine and dried over sodium sulphate, filtered and concentrated to get the crude product which was purified as yellow solids (100 mg, 9%) by flash column chromatography on neutral silica gel using chloroform as eluent.

5.5 2-(3,5-Dimethyl-piperidin-1-ylmethyl)-1-aza-bicyclo[2.2.2]octan-3-one

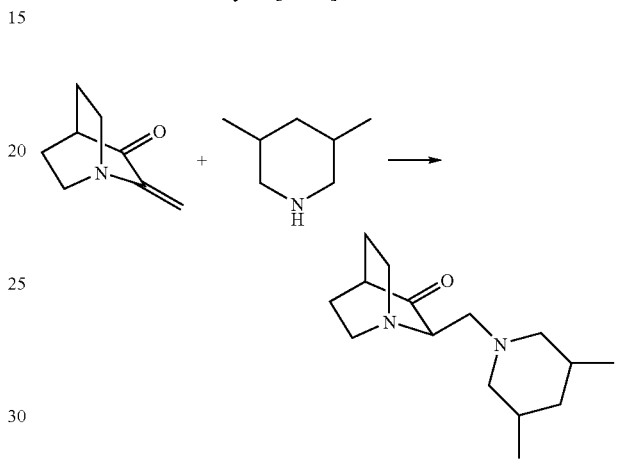

To a stirred solution of 2-methylene-3-quinuclidinone hydrochloride (0.25 g, 0.0014 mol) in water (5 ml) 3,5-dimethylpiperidine (0.32 g, 0.0028 mol), triethylamine (0.84 g, 0.0084 mol) and tetra-n-butyl ammonium bromide (45 mg, 0.00014 mol) were added and the reaction mixture were allowed to stir at 80° C. for 18 h. The completion of reaction was monitored by tlc. The reaction mixture was quenched with ice-cold water (20 ml), extracted with dichloromethane (3×50 ml), the organic layers were washed with brine and dried over sodium sulphate, filtered and concentrated to get the crude product which was purified (100 mg) by flash column chromatography on neutral silica gel using chloroform as eluent.

Example 6

Method for alkoxylation (or aroxylation) of 2-methylene-1-aza-bicyclo[2.2.2]octan-3-one (8)

6.1 2-Propoxymethyl-1-aza-bicyclo[2.2.2]octan-3-one

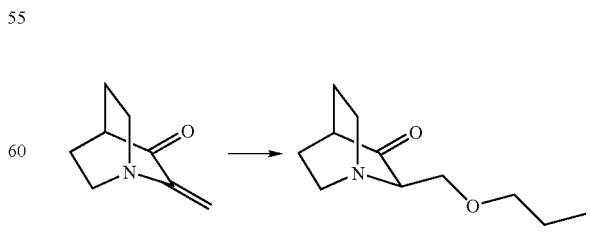

To a stirred solution of 2-methylene-3-quinuclidinone (100 mg) in dry dichloromethane (5 ml) propanol (1 equiv., 0.04 ml) was added in presence of molecular sieves (4 Å). The reaction mixture was stirred at RT for overnight. The reaction mixture was filtered and the filtrate was concentrate to get crude product, which was purified (70 mg, 50%) by column chromatography on silica gel using 0.5% methanol in chloroform as eluent.

Example 7

Method for formation of thioethers of 2-methylene-1-aza-bicyclo[2.2.2]octan-3-one (8)

7.1 2-(9H-Purin-6-ylsulfanylmethyl)-1-aza-bicyclo [2.2.2]octan-3-one

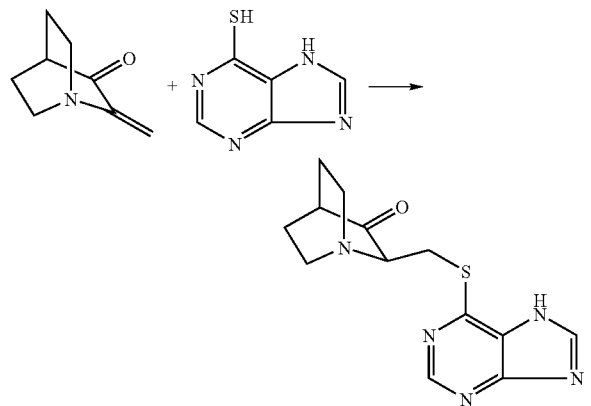

To a stirred solution of 2-methylene-3-quinuclidinone hydrochloride (0.5 g, 3.6 mmol) in water (6 ml) triethylamine (1.5 ml), tetra-n-butyl ammonium bromide (120 mg) and 6-mercapto-purine monohydrate (0.62 g) were added and the reaction mixture was allowed to stir at 85° C. for 14 h. The completion of reaction was monitored by tlc. The reaction mixture was quenched with ice-cold water (10 ml), extracted with dichloromethane (2×25 ml), the organic layers were washed with water, brine and dried over sodium sulphate, filtered and concentrated to get the crude product which was purified (140 mg, 14%) by flash column chromatography on neutral silica gel using 9:1 chloroform:methanol as eluent.

7.2 (RS)-2-Phenylsulfanylmethyl-1-aza-bicyclo [2.2.2]octan-3-one

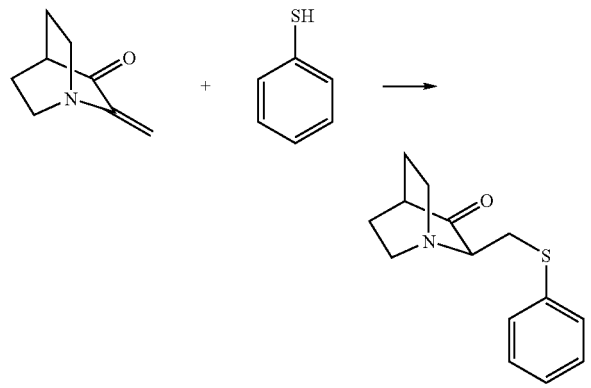

To a stirred solution of 2-methylene-3-quinuclidinone hydrochloride (1 g, 0.0057 mol) in water (10 ml) triethylamine (1.73 g, 0.0171 mol), tetra-n-butyl ammonium bromide (180 mg, 0.00057 mol) and thiophenol (0.63 g, 0.0057 mol) were added and the reaction mixture was allowed to stir at 80° C. for 18 h. The completion of reaction was monitored by tlc. The reaction mixture was quenched with ice-cold water (20 ml), extracted with dichloromethane (4×50 ml), organic layers were washed with brine and dried over sodium sulphate, filtered and concentrated to get the crude product which was purified (550 mg) by column chromatography on silica gel using chloroform as eluent.

Example 8

Method for formation of carbamates of 2,2-bis-hydroxymethyl-1-aza-bicyclo[2.2.2]octan-3-one (2)

8.1 Pyrrolidine-carbamic acid 2-[(Pyrrolidine-carbamoyloxy)-methyl]-3-oxo-1-aza-bicyclo[2.2.2]oct-2-ylmethyl ester

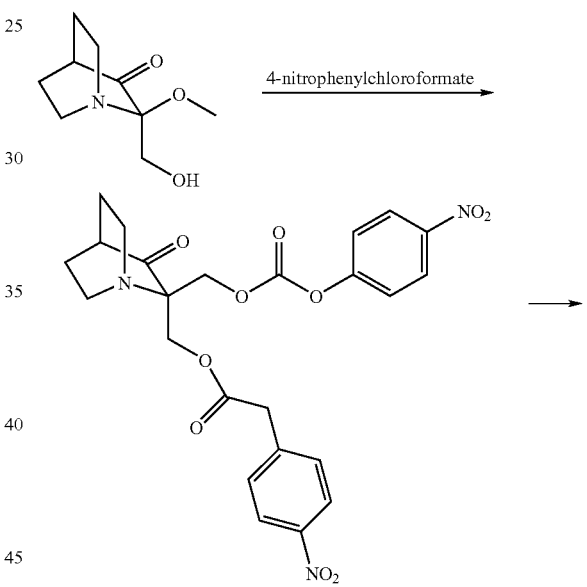

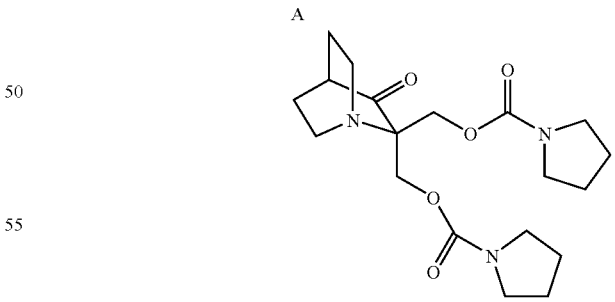

To a stirred solution of bismethylol of 3-quinuclidinone (1 g, 0.0054 mol) in dry THF (40 ml) pyridine (0.93 g, 0.0118 mol) was added under nitrogen atmosphere. The reaction mixture was cooled to 5° C. A solution of 4-nitrophenylchloroformate (2.2 g, 0.0113 mol) in dry THF (10 ml) was added slowly at 5° C. and stirring was continued for 18 h at room temperature (26-27° C.). The reaction mixture was quenched with 10% aqueous NaHCO$_3$ solution (100 ml), extracted with dichloromethane (3×100 ml), the organic layers were washed with brine and dried over sodium sulphate, filtered and concentrated to get the crude product, which was purified as yellow solids intermediate A (400 mg, 15%) by column chromatography on silica gel using chloroform as eluent.

To a stirred solution of pyrrolidine (28 mg, 0.0004 mol) in pyridine (5 ml) the intermediate A (100 mg, 0.00019 mol) was added at −5° C. under nitrogen atmosphere. The reaction mixture was allowed to stir at RT for 15 h. Excess pyridine was removed under vacuum. The reaction mixture was then quenched with ice-water (20 ml), extracted with dichloromethane (3×50 ml), dried over sodium sulphate, filtered and concentrated to get the crude product which was purified (40 mg, 57%) by column chromatography on silica gel using 0.1% methanol in chloroform as eluent.

8.2 Bis-(2-chloro-ethyl)-carbamic acid 2-{[bis-(2-chloro-ethyl)-carbamoyloxy]-methyl}-3-oxo-1-aza-bicyclo[2.2.2]oct-2-ylmethyl ester

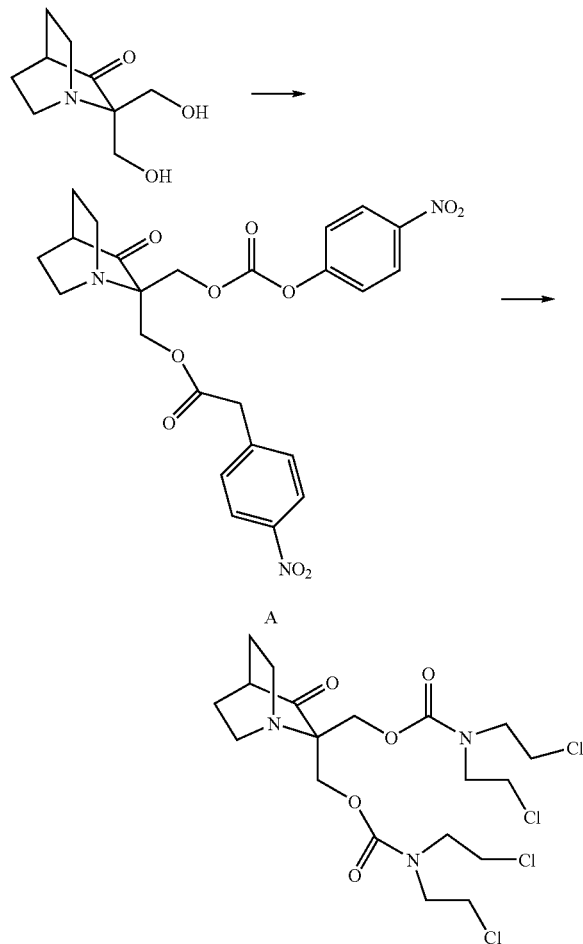

To a stirred solution of bismethylol of 3-quinuclidinone (2 g, 0.0108 mol) in dry THF (100 ml) pyridine (1.8 ml, 0.0236 mol) was added under nitrogen atmosphere. The reaction mixture was cooled to −5° C. A solution of 4-nitrophenyl-chloroformate (4.4 g, 0.0226 mol) in dry THF (50 ml) was added slowly at −5° C. and stirring was continued for 12 h at room temperature (26-27° C.). The reaction mixture was quenched with 10% aqueous $NaHCO_3$ solution (100 ml) and extracted with dichloromethane (3×100 ml). The organic layers were washed with water, brine and dried over sodium sulphate, filtered and concentrated to get the crude product, which was purified by recrystallisation to get pure intermediate A (560 mg, 10%).

To a stirred solution of bis(2-chloroethyl)amine hydrochloride (430 mg) in pyridine (20 ml) the intermediate A (400 mg) was added at 0° C. under nitrogen atmosphere. The reaction mixture was allowed to stir at RT for 10 h. Excess pyridine was removed under vacuum, then quenched with ice-water (20 ml), extracted with dichloromethane (3×25 ml), organic layers were washed with brine, dried over sodium sulphate, filtered and concentrated to get the crude product which was purified (190 mg, 47%) by column chromatography on silica gel using 1% methanol in chloroform as eluent.

8.3 Dimethyl-carbamic acid 2-dimethylcarbamoyloxymethyl-3-oxo-1-aza-bicyclo[2.2.2]oct-2-ylmethyl ester

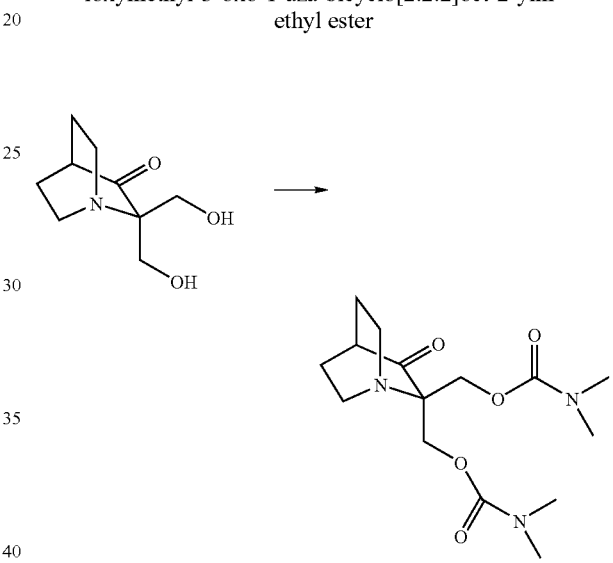

To a stirred solution of bismethylol of 3-quinuclidinone (1 g, 0.0054 mol) in dry dichloromethane (50 ml) pyridine (2.5 g, 0.0318 mol) was added and the reaction mixture was cooled to 5° C. N,N-dimethyl carbonyl chloride (1.45 g, 0.0134 mol) was added slowly at 5° C. under nitrogen and stirring was continued for another 30 minutes. The reaction mixture was warmed up to RT and stirred for 19 h. The reaction mixture was quenched with ice-cold water (50 ml), extracted with dichloromethane (3×50 ml), washed with water, brine and dried over sodium sulphate, filtered and concentrated to get the crude product which was purified (125 mg) by column chromatography on silica gel using 0.5:99.5 methanol:chloroform as eluent.

Biology Tests

The human H1299-His175 lung carcinoma cell line that carries a tetracycline-regulated mutant p53 construct was used for studying the antiproliferative and apoptosis inducing effects of the present compounds.

WST-1 Assay Protocol

Cell Culture

Cells were cultured in Iscove's Modified Dulbecco's Medium supplemented with 10% fetal bovine serum, L-glutamine and gentamycin.

Seeding of Cells

Cells were taken out for experiment when they were at about 75-100% confluent. After trypsinization, cells were diluted to a cell concentration of 30 000 cells/ml in cell culture medium. Cells were placed in 96-wells plates with flat bottom at 100 µl/well (3000 cells/well). The last column of the plate was filled with medium alone, 100 µl/well, to use as blank. Cells were then incubated over night in the cell incubator.

Treatment of Cells

After about 16-24 hours of incubation in 96-wells plates, the cells were treated with the different compounds. The drugs were dissolved in DMSO at a concentration of 0.1 M and then further diluted to desired concentrations in PBS. 5 µl of each compound was then added to each well. One column of cells was usually left untreated as control. Cell plates were put back in the cell incubator.

Addition of WST-1 Reagent

After 96 hours in the cell incubator, the WST-1 reagent was added to the plates. 10 µl of reagent was added to each well of the plates (including untreated cells and wells with medium alone). The absorbance of the samples was measured in a spectrophotometer at 450 nm after about 1-2 hours of incubation in the cell incubator. Before reading the plates, they were checked visually by comparing the color in the wells with medium alone and the color in wells with untreated cells. The medium should remain red-pink in color whereas the untreated cells should switch from red-pink to orange.

Analysis of WST-1

The average of the absorbance values for the untreated cells was calculated for each plate. The % of growth suppression was calculated as: $100-((Abs_{sample}/Abs_{untreated\ cells}) \times 100)$.

The results of WST-1 analyses are expressed as IC50 values, i.e. concentration that suppresses growth of at least 50% of the cells. The IC50 values of various compounds according to the invention, as well as of one reference compound not according to the invention, are shown in Table 1. In those cases where the compound according to the invention has been tested in the form of an acid addition salt the corresponding acid is shown in Table 1.

TABLE 1

Examples of tested compounds and IC50 values from WST-1 assay

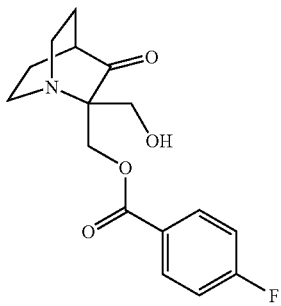

12.5 µM

TABLE 1-continued

Examples of tested compounds and IC50 values from WST-1 assay

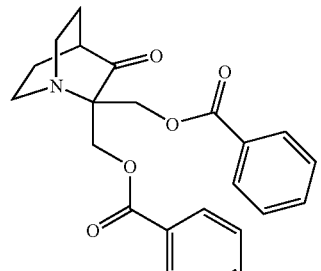

19.3 µM

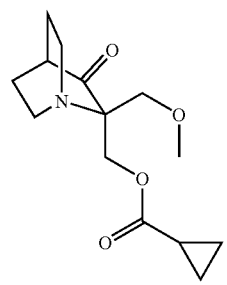

38 µM

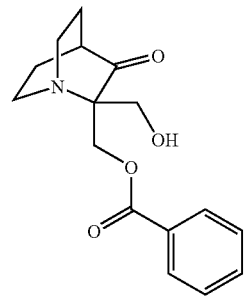

20.0 µM

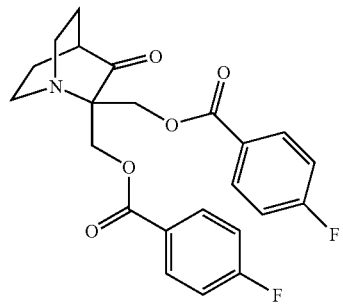

14.2 µM

TABLE 1-continued
Examples of tested compounds and IC50 values from WST-1 assay
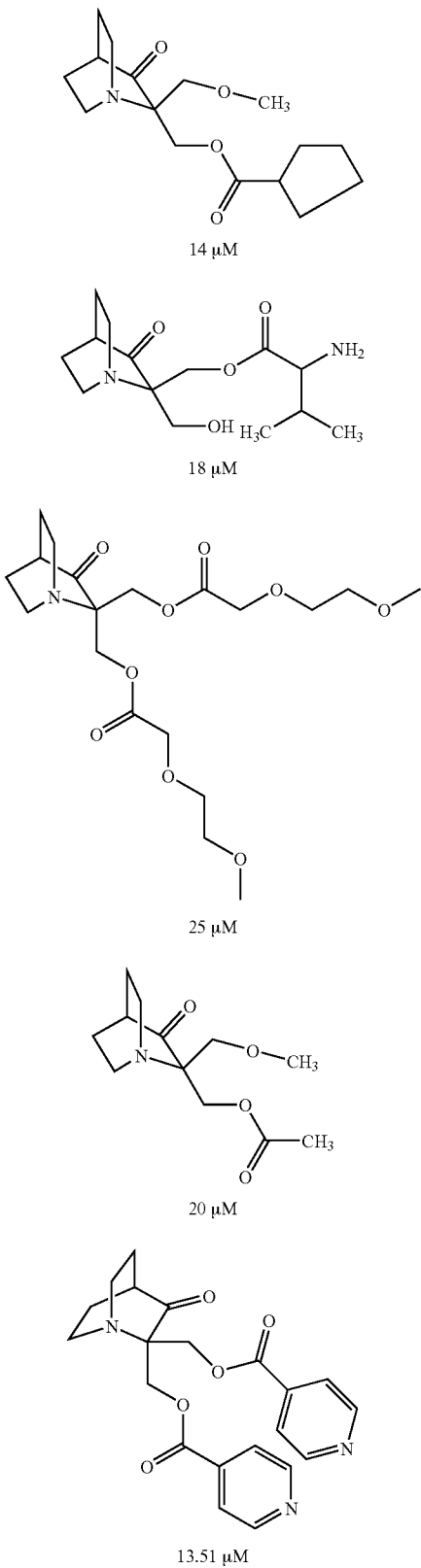
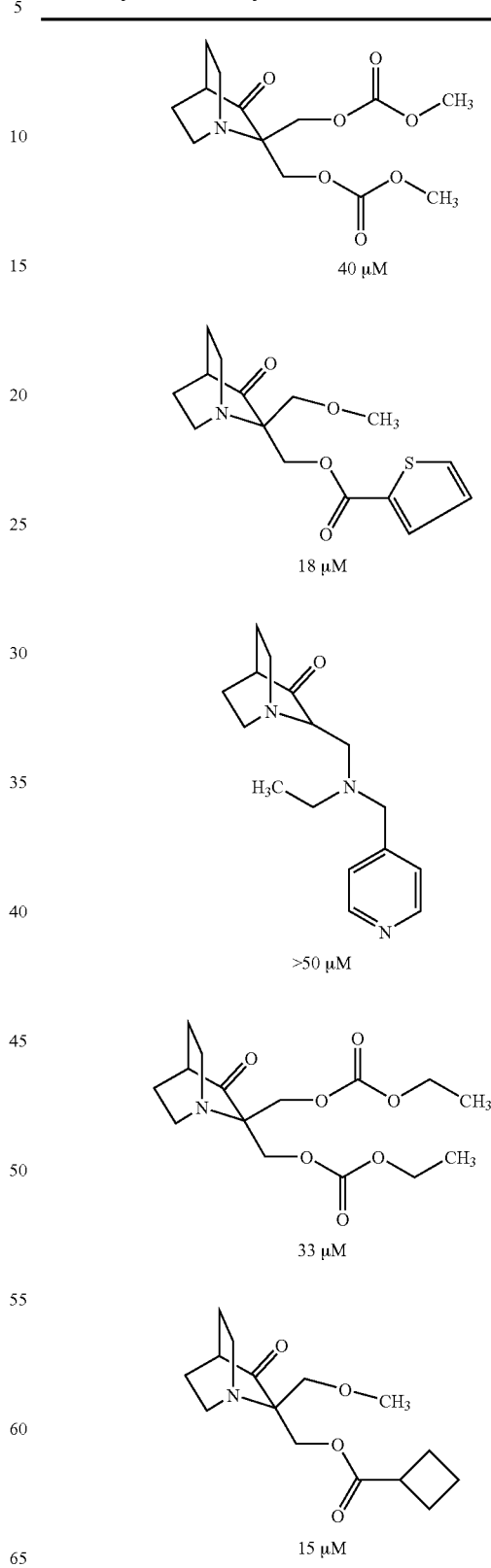

TABLE 1-continued
Examples of tested compounds and IC50 values from WST-1 assay
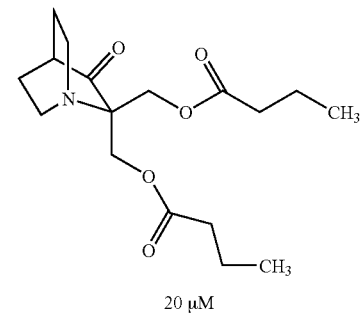
20 µM
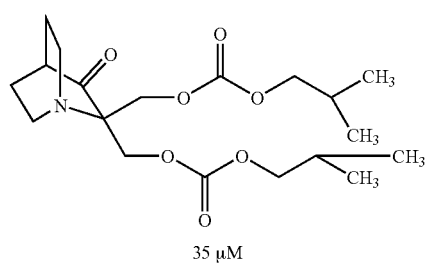
35 µM
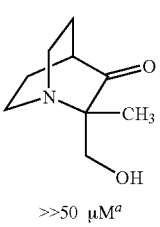
>>50 µM[a]
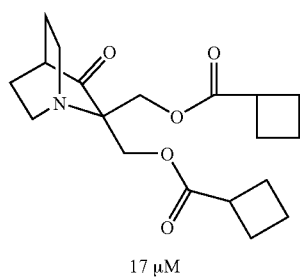
17 µM
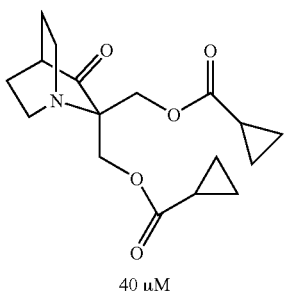
40 µM
TABLE 1-continued
Examples of tested compounds and IC50 values from WST-1 assay
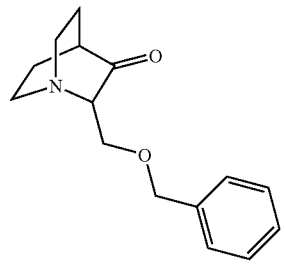
8.5 µM
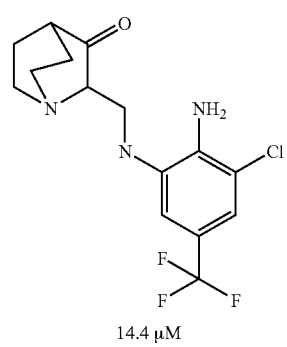
14.4 µM
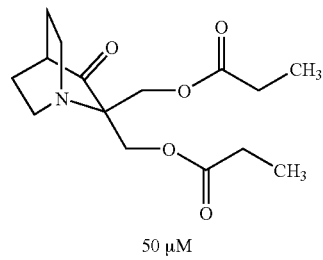
50 µM
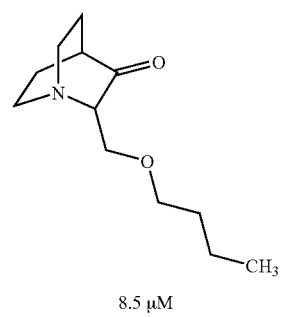
8.5 µM
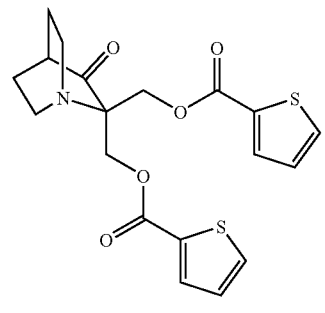
33.0 µM TABLE 1-continued
Examples of tested compounds and IC50 values from WST-1 assay
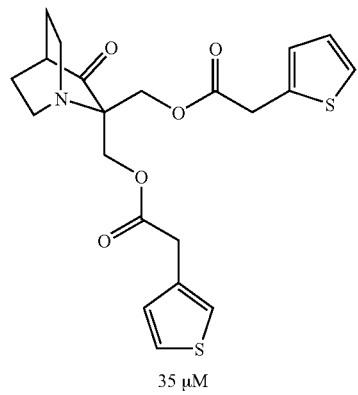
35 μM
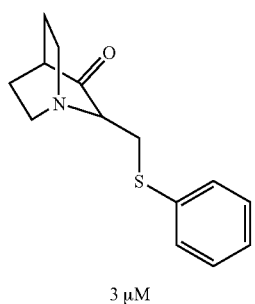
3 μM
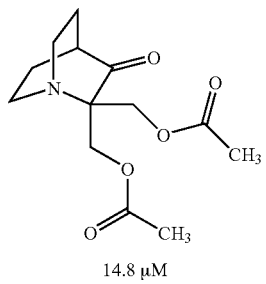
14.8 μM
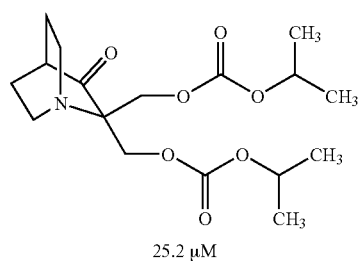
25.2 μM
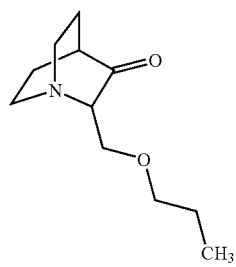
8.6 μM
TABLE 1-continued
Examples of tested compounds and IC50 values from WST-1 assay
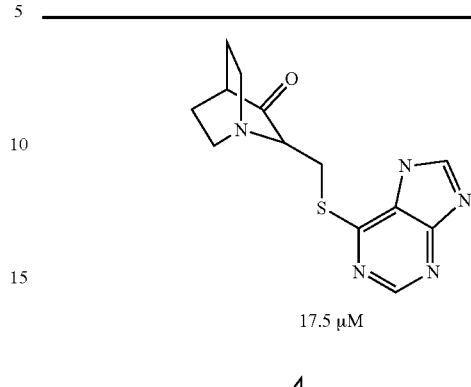
17.5 μM
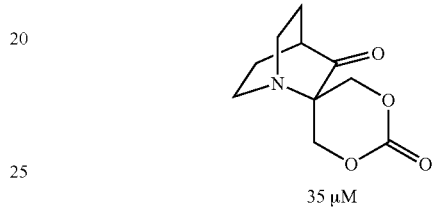
35 μM
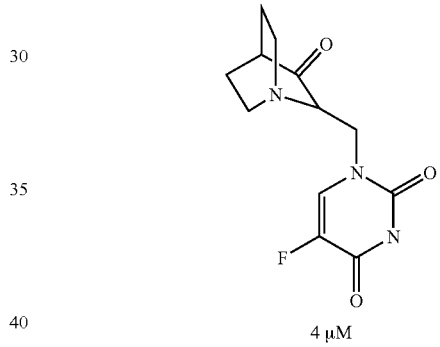
4 μM
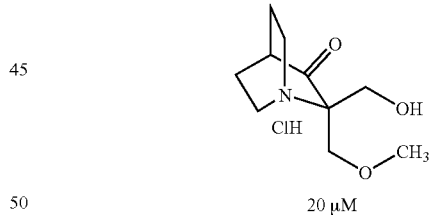
20 μM
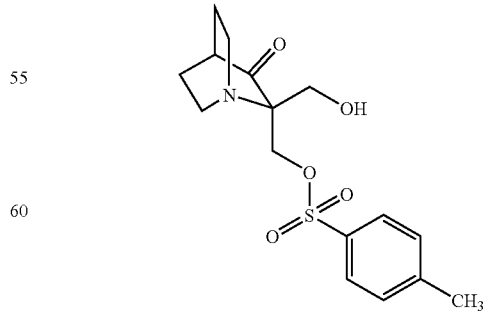
6.3 μM TABLE 1-continued
Examples of tested compounds and IC50 values from WST-1 assay
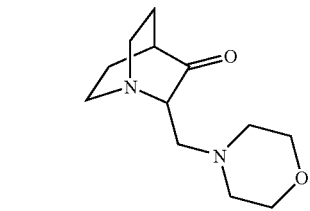
6.8 µM
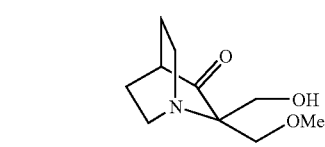
17 µM
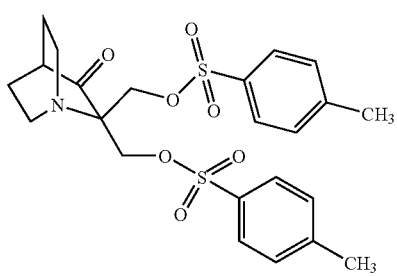
>50 µM
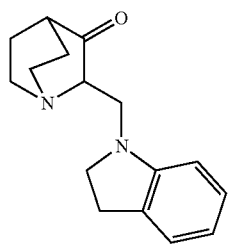
3.3 µM
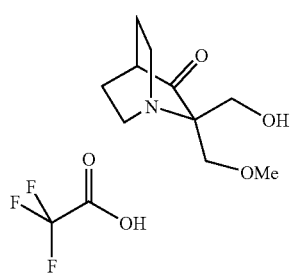
25 µM
TABLE 1-continued
Examples of tested compounds and IC50 values from WST-1 assay
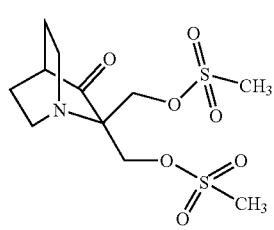
50 µM
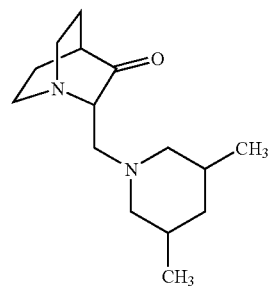
6.2 µM
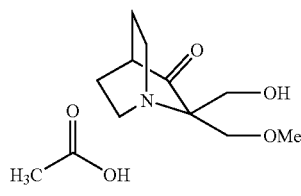
17 µM
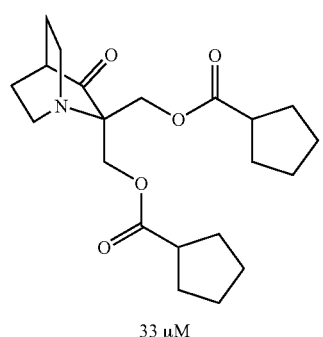
33 µM
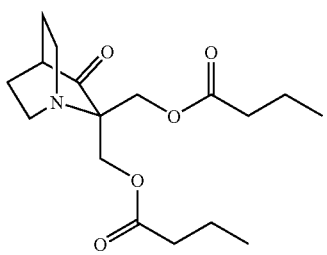
20 µM TABLE 1-continued
Examples of tested compounds and IC50 values from WST-1 assay
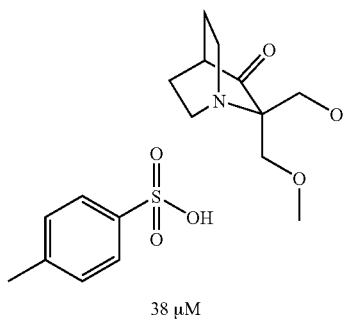
38 μM
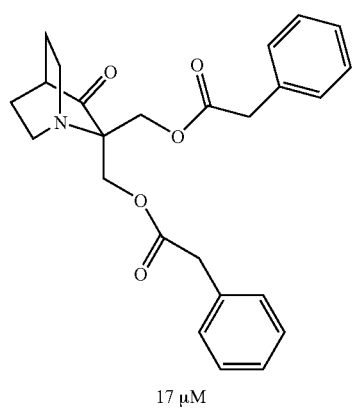
17 μM
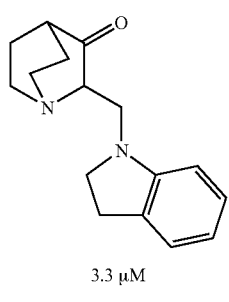
3.3 μM
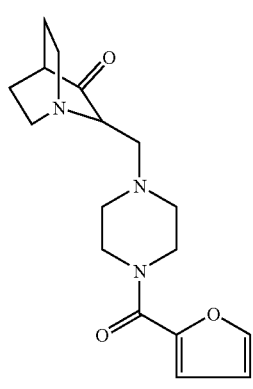
13 μM
TABLE 1-continued
Examples of tested compounds and IC50 values from WST-1 assay
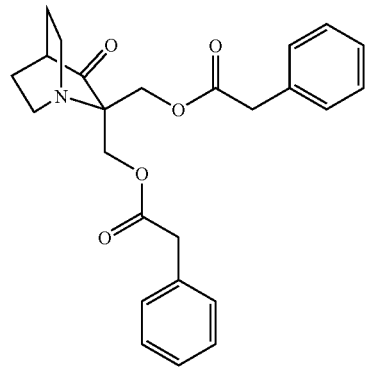
35 μM
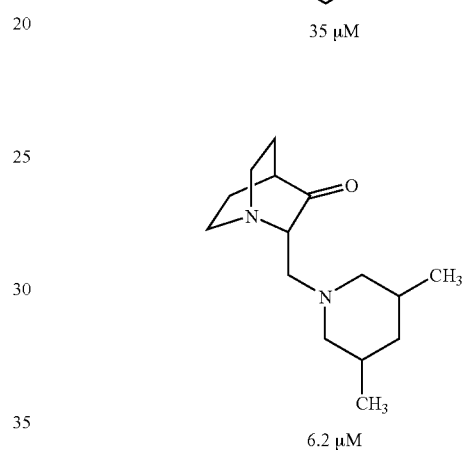
6.2 μM
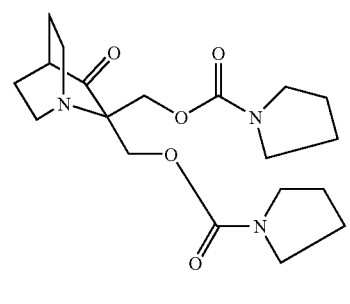
>50 μM
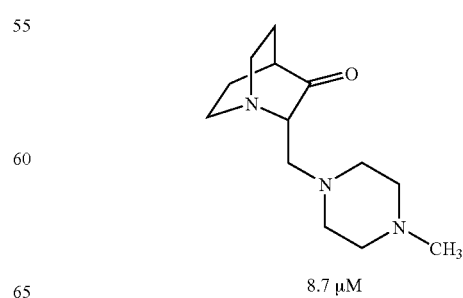
8.7 μM

TABLE 1-continued

Examples of tested compounds and IC50 values from WST-1 assay

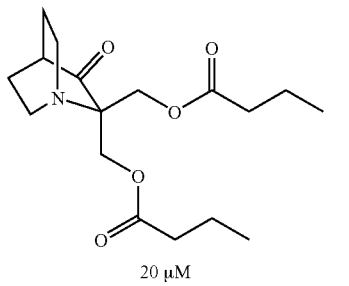

20 μM

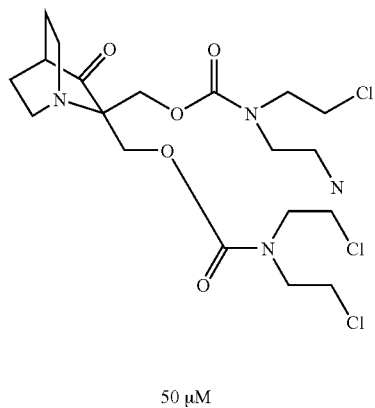

50 μM

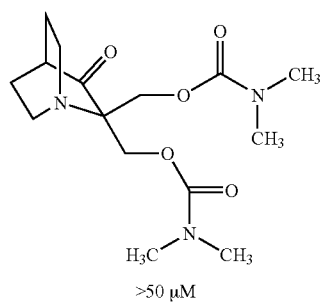

>50 μM

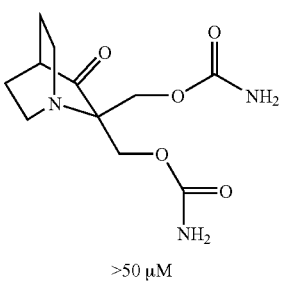

>50 μM

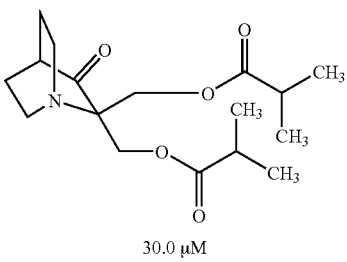

30.0 μM

*a* Compound not according to the invention

FACS Analysis

H1299-His175 cells were plated in 6-wells plates at the initial density of 10,000 cells/cm², cultured overnight and treated with compounds of the invention. After 24 hours of treatment, the medium containing floating cells was collected and pooled with harvested adherent cells. The cells were washed once in PBS and resuspended in 200 ul PBS. Ice-cold 70% ethanol was added while vortexing and the cells were stored at −20° C. for 24 hours. Fixed cells were then collected by centrifugation, washed once in PBS and incubated in 100 μl PI staining buffer (5 μg/ml PI and 250 μg/ml RNaseA) for 30 minutes in 37° C. Samples were assayed using a FACS-Calibur flow cytometer and the sub $G_0/G_1$ peak quantified using CELLQuest software. Results obtained with compounds according to the invention are shown in the Figure.

REFERENCES

Bardeesy et al., *Cancer Res* 55, 215-9 (1995).
Bennett, M., et al. *Science* 282, 290-293 (1998).
Béroud, C. & Soussi, T., *Nucl. Acids Res.* 26, 200-204 (1998).
Biel et al. U.S. Pat. No. 3,384,641
Biel et al. U.S. Pat. No. 3,462,442
Biel et al. U.S. Pat. No. 3,598,825
Evan, G. & Littlewood, T., *Science.* 281, 1317-1322 (1998).
Elkin et al. U.S. Pat. No. 3,726,877
Gottlieb and Oren, *Semin Cancer Biol* 8, 359-68 (1998),
Ko, L. J. & Prives, C., *Genes Dev.* 10, 1054-1072 (1996).
Lowe et al., 1994 *Science* 266, 807-10 (1994).
Morgan et al., *J. Med. Chem.* 30, 2559-2569 (1987).
Nielsen et al., *J. Org. Chem.* 31, 1053-1057 (1966).
Sakamuri et al., *Tetrahedron Lett.* 41, 9949-9952 (2000).
Sampath Kumar et al., *Tetrahedron Lett.* 38, 3619-3622 (1997).
Schieweck et al, *J. Chem. Soc., Perkin Trans.* 1, 3409-3414 (2001).
Sherr, C. J., *Genes Dev.* 12, 2984-2991 (1998).
Singh et al., *J. Med. Chem.* 12, 524-526 (1969).
Symonds et al., *Cell* 78, 703-711 (1994).
Toender et al, *Tetrahedron.* 56, 1139-1146 (2000).
WO 02/24692
WO 03/070250

The invention claimed is:

1. A method of treating a cancer comprising:
administering, to a patient in need thereof, an effective amount of a compound of formula (I)

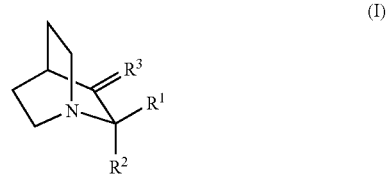

(I)

wherein
(i) $R^1$ and $R^2$ are the same or different and are selected from H, —CH$_2$—O—R$^5$, —CH$_2$—O—SO$_2$—R$^5$, —CH$_2$—S—R$^5$, —CH$_2$—O—CO—R$^5$, —CH$_2$—O—CO—NR$^4$R$^5$ and —CH$_2$—O—CO—OR$^5$;
$R^3$ is =O;
$R^4$ and $R^5$ are the same or different and are selected from H; substituted or non-substituted, unbranched or branched, saturated or unsaturated C3-C12 cycloalkyl or C1-C10 alkyl; substituted or non-substituted benzyl; substituted or non-substituted mono- or bicyclic aryl; substituted or non-substituted mono-, bi- or tricyclic C1-C10 heteroaryl or non-aromatic C1-C10 heterocyclyl wherein the heteroatoms are independently selected from N, O and S; or $R^4$ and $R^5$ in —$NR^4R^5$ are bonded together and form, together with the nitrogen atom to which they are bonded, a substituted or non-substituted non-aromatic C1-C10 mono- or bicyclic heterocyclyl optionally containing one or several further heteroatoms independently selected from N, O and S and optionally comprising one or several cyclic keto groups;

with the proviso that when $R^1$ and $R^2$ are both —$CH_2$—$OR^5$ then both $R^5$ are not H; and with the further proviso that $R^1$ and $R^2$ are not both H; or (ii) $R^1$ and $R^2$ together with the carbon atom to which they are bonded form an substituted or non-substituted cyclic carbonate; wherein the substituents of the substituted groups are selected from unbranched or branched, saturated or unsaturated C3-C12 cycloalkyl or C1-C10 a alkyl; halogen; mono- or bicyclic aryl; mono-, bi- or tricyclic C1-C10 a heteroaryl and non-aromatic C1-C10 a heterocyclyl wherein the heteroatoms are independently selected from N, O and S; C1-C10 a alkyloxy; amino; C1-C10 a alkylamino; $COR^6$; $CONR^6R^7$; and $COOR^6$;

$R^6$ and $R^7$ are the same or different and are selected from H; unbranched or branched, saturated or unsaturated C3-C12 cycloalkyl or C1-C10 a alkyl; benzyl; mono- or bicyclic aryl; mono-, bi- or tricyclic heteroaryl or non-aromatic C1-C10 heterocyclyl wherein the heteroatoms are independently selected from N, O and S; or a pharmaceutically acceptable salt thereof.

2. A process for the preparation of a compound of formula (I)

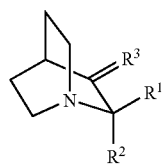

wherein (i) $R^1$ and $R^2$ are the same or different and are selected from H, —$CH_2OH$, —$CH_2$—O—CO—$R^5$, —$CH_2$—O—CO—$NR^4R^5$ and —$CH_2$—O—CO—$OR^5$;

$R^3$ is =O;

$R^4$ and $R^5$ are the same or different and are selected from H; substituted or non-substituted, unbranched or branched, saturated or unsaturated C3-C12 cycloalkyl or C10-C10 alkyl; substituted or non-substituted benzyl; substituted or non-substituted mono- or bicyclic aryl; substituted or non-substituted mono-, bi- or tricyclic C1-C10 heteroaryl or non-aromatic C1-C10 heterocyclyl wherein the heteroatoms are independently selected from N, O and S; or $R^4$ and $R^5$ in —$NR^4R^5$ are bonded together and form, together with the nitrogen atom to which they are bonded, a substituted or non-substituted non-aromatic C1-C10 mono- or bicyclic heterocyclyl optionally containing one or several further heteroatoms independently selected from N, O and S and optionally comprising one or several cyclic keto groups;

with the proviso that $R^1$ and $R^2$ are not both selected from H and —$CH_2OH$; or (ii) $R^1$ and $R^2$ together with the carbon atom to which they are bonded form a substituted or non-substituted cyclic carbonate; wherein the substituents of the substituted groups are selected from unbranched or branched, saturated or unsaturated C3-C12 cycloalkyl or C1-C10 alkyl; halogen; mono- or bicyclic aryl; mono-, bi- or tricyclic C1-C10 heteroaryl or non-aromatic C1-C10 heterocyclyl wherein the heteroatoms are independently selected from N, O and S; C1-C10 alkyloxy; amino; C1-C10 alkylamino; $COR^6$; $CONR^6R^7$; and $COOR^6$;

$R^6$ and $R^7$ are the same or different and are selected from H; unbranched or branched, saturated or unsaturated C3-C12 cycloalkyl or C1-C10 alkyl; benzyl; mono- or bicyclic aryl; mono-, bi- or tricyclic heteroaryl or non-aromatic C1-C10 heterocyclyl wherein the hetero-atoms are independently selected from N, O and S; or a pharmaceutically acceptable salt of the compound of formula (I), said process comprising reacting a compound of said formula (I)

wherein at least one of $R^1$ and $R^2$ is —$CH_2OH$; or wherein both $R^1$ and $R^2$ are —$CH_2$;

with a compound of formula $R^5$—CO—X, $NR^4R^5$—CO—X, or $R^5O$—CO—X; wherein X is a leaving group; under conditions suitable for transforming at least one of $R^1$ and $R^2$ into —$CH_2$—O—CO—$R^5$, —$CH_2$—O—CO—$NR^4R^5$ or —$CH_2$—O—CO—$OR^5$;

or by reacting a compound of said formula (I) wherein both $R^1$ and $R^2$ are —$CH_2OH$; with a compound of formula

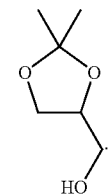

3. A of formula (I)

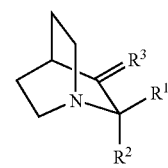

wherein (i) $R^1$ and $R^2$ are the same or different and are selected from H, —$CH_2OH$, —$CH_2$—O—CO—$R^5$, —$CH_2$—O—CO—$NR^4R^5$ and —$CH_2$—O—CO—$OR^5$;

$R^3$ is =O;

$R^4$ and $R^5$ are the same or different and are selected from H; substituted or non-substituted, unbranched or branched, saturated or unsaturated C3-C12 cycloalkyl or C1-C10 alkyl; substituted or non-substituted benzyl; substituted or non-substituted mono- or bicyclic aryl; substituted or non-substituted mono-, bi- or tricyclic C1-C10 heteroaryl or non-aromatic C1-C10 heterocyclyl wherein the heteroatoms are independently selected from N, O and S; or $R^4$ and $R^5$ in —$NR^4R^5$ are bonded together and form, together with the nitrogen atom to which they are bonded, a substituted or non-substituted non-aromatic C1-C10 mono- or bicyclic heterocyclyl optionally containing one or several further heteroatoms independently selected from N, O and S and optionally comprising one or several cyclic keto groups;

with the proviso that $R^1$ and $R^2$ are not both selected from H and —$CH_2OH$; or (ii) $R^1$ and $R^2$ together with the carbon atom to which they are bonded form a substituted or non-substituted cyclic carbonate; wherein the substituents of the substituted groups are selected from unbranched or branched, saturated or unsaturated C3-C12 cycloalkyl or C1-C10 alkyl; halogen; mono- or bicyclic aryl; mono-, bi- or tricyclic C1-C10 heteroaryl or non-aromatic C1-C10 heterocyclyl wherein the heteroatoms are independently selected from N, O and S; C1-C10 alkyloxy; amino; C1-C10 alkylamino; $COR^6$; $CONR^5R^7$; and $COOR^6$;

$R^6$ and $R^7$ are the same or different and are selected from H; unbranched or branched, saturated or unsaturated C3-C12 cycloalkyl or C1-C10 alkyl; benzyl; mono- or bicyclic aryl; mono-, bi- or tricyclic heteroaryl or non-aromatic C1-C10 heterocyclyl wherein the hetero-atoms are independently selected from N, O and S; or a pharmaceutically acceptable salt of the compound of formula (I), for use as a medicament.

4. A pharmaceutical composition comprising a therapeutically effective amount of a compound of formula (I)

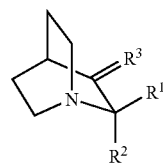

(I)

wherein (i) $R^1$ and $R^2$ are the same or different and are selected from H, —$CH_2OH$, —$CH_2$—O—CO—$R^5$, —$CH_2$—O—CO—$NR^4R^5$ and —$CH_2$—O—CO—$OR^5$;

$R^3$ is =O;

$R^4$ and $R^5$ are the same or different and are selected from H; substituted or non-substituted, unbranched or branched, saturated or unsaturated C3-C12 cycloalkyl or C1-C10 alkyl; substituted or non-substituted benzyl; substituted or non-substituted mono- or bicyclic aryl; substituted or non-substituted mono-, bi- or tricyclic C1-C10 heteroaryl or non-aromatic C1-C10 heterocyclyl wherein the heteroatoms are independently selected from N, O and S; or $R^4$ and $R^5$ in —$NR^4R^5$ are bonded together and form, together with the nitrogen atom to which they are bonded, a substituted or non-substituted non-aromatic C1-C10 mono- or bicyclic heterocyclyl optionally containing one or several further heteroatoms independently selected from N, O and S and optionally comprising one or several cyclic keto groups;

with the proviso that $R^1$ and $R^2$ are not both selected from H and —$CH_2OH$; or (ii) $R^1$ and $R^2$ together with the carbon atom to which they are bonded form a substituted or non-substituted cyclic carbonate; wherein the substituents of the substituted groups are selected from unbranched or branched, saturated or unsaturated C3-C12 cycloalkyl or C1-C10 alkyl; halogen; mono- or bicyclic aryl; mono-, bi- or tricyclic C1-C10 heteroaryl or non-aromatic C1-C10 heterocyclyl wherein the heteroatoms are independently selected from N, O and S; C1-C10 alkyloxy; amino; C1-C10 alkylamino; $COR^5$; $CONR^6R^7$; and $COOR^6$;

$R^6$ and $R^7$ are the same or different and are selected from H; unbranched or branched, saturated or unsaturated C3-C12 cycloalkyl or C1-C10 alkyl; benzyl; mono- or bicyclic aryl; mono-, bi- or tricyclic heteroaryl or non-aromatic C1-C10 heterocyclyl wherein the hetero-atoms are independently selected from N, O and S; or a pharmaceutically acceptable salt thereof; and at least one pharmaceutically acceptable excipient.

5. A pharmaceutical composition according to claim 4, comprising at least one further, pharmaceutically active compound.

6. A pharmaceutical composition according to claim 5, wherein the at least one further active compound in vivo is susceptible of reacting with glutathione.

7. A pharmaceutical composition according to claim 5 or claim 6, wherein the at least one further pharmaceutically active compound is selected from the group consisting of adriamycin, melphalan and cisplatin.

8. A method of treating a cancer comprising:
administering, to a patient in need thereof, a therapeutically effective amount of a compound of formula (I)

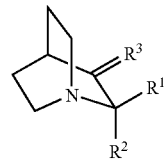

(I)

wherein (i) $R^1$ and $R^2$ are the same or different and are selected from H, —$CH_2$—O—$R^5$, —$CH_2$—O—$SO_2$—$R^5$, —$CH_2S$—$R^5$, —$CH_2$—O—CO—$R^5$, —$CH_2$—O—CO—$NR^4R^5$ and —$CH_2$—O—CO—$OR^5$;

$R^3$ is =O;

$R^4$ and $R^5$ are the same or different and are selected from H; substituted or non-substituted, unbranched or branched, saturated or unsaturated C3-C12 cycloalkyl or C1-C10 alkyl; substituted or non-substituted benzyl; substituted or non-substituted mono- or bicyclic aryl; substituted or non-substituted mono-, bi- or tricyclic C1-C10 heteroaryl or non-aromatic C1-C10 heterocyclyl wherein the heteroatoms are independently selected from N, O and S; or $R^4$ and $R^5$ in —$NR^4R^5$ are bonded together and form, together with the nitrogen atom to which they are bonded, a substituted or non-substituted non-aromatic C1-C10 mono or bicyclic heterocyclyl optionally containing one or several further heteroatoms independently selected from N, O and S and optionally comprising one or several cyclic keto groups;

with the proviso that when $R^1$ and $R^2$ are both —$CH_2$—$OR^5$ then both $R^5$ are not H; and with the further proviso that when one of $R^1$ and $R^2$ is H and the other one is —$CH_2$—$NR^4R^5$, then $R^4$ and $R^5$ are not substituted or non-substituted monocyclic aryl; or (ii) $R^1$ and $R^2$ together with the carbon atom to which they are bonded form a substituted or non-substituted cyclic carbonate; wherein the substituents of the substituted groups are selected from unbranched or branched, saturated or unsaturated C3-C12 cycloalkyl or C1-C10 alkyl; halogen; mono or bicyclic aryl; mono-, bi- or tricyclic C1-C10 heteroaryl or non-aromatic C1-C10 heterocyclyl wherein the heteroatoms are independently selected from N, O and S; C1-C10 alkyloxy; amino; C1-C10 alkylamino; COR$^6$; CONR$^6$R$^7$; and COOR$^6$;

R$^6$ and R$^7$ are the same or different and are selected from H; unbranched or branched, saturated or unsaturated C3-C12 cycloalkyl or C1-C10 alkyl; benzyl; mono- or bicyclic aryl; mono-, bi- or tricyclic heteroaryl or non-aromatic C1-C10 heterocyclyl wherein the heteroatoms are independently selected from N, O and S; or a pharmaceutically acceptable salt thereof.

9. The method according to claim 8, wherein the compound of formula (I) is administered together with at least one further, pharmaceutically active compound.

10. The method according to the claim 9 wherein, the at least one further pharmaceutically active compound in vivo is susceptible of reacting with glutathione.

11. The method according to claim 9 or claim 10, wherein the at least one further pharmaceutically active compound is selected from the group consisting of adriamycin, melphalan, and cisplatin.

12. A method of treating a mammal suffering from a cancer,
comprising administering to said mammal in need thereof a therapeutically effective amount of a compound selected from the group consisting of:

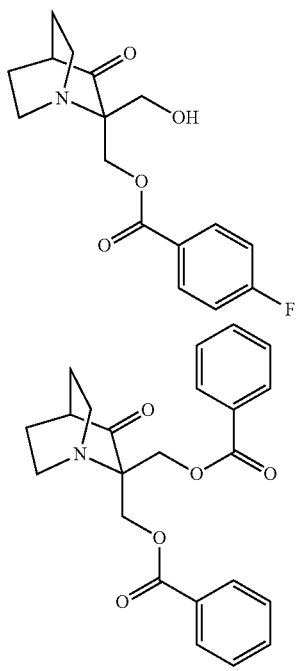

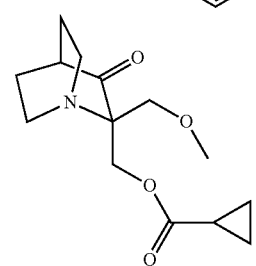

-continued

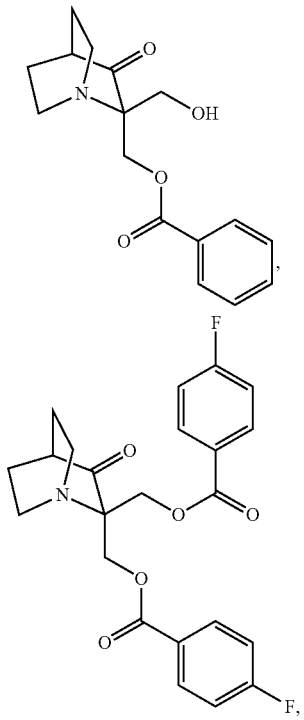

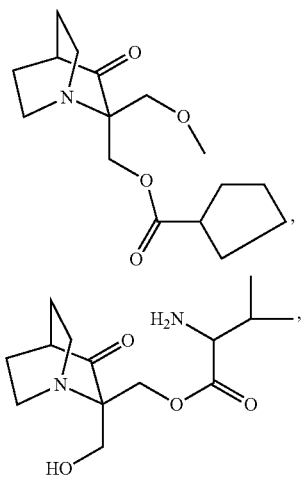

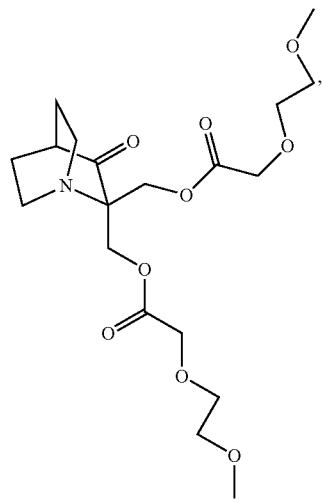

-continued
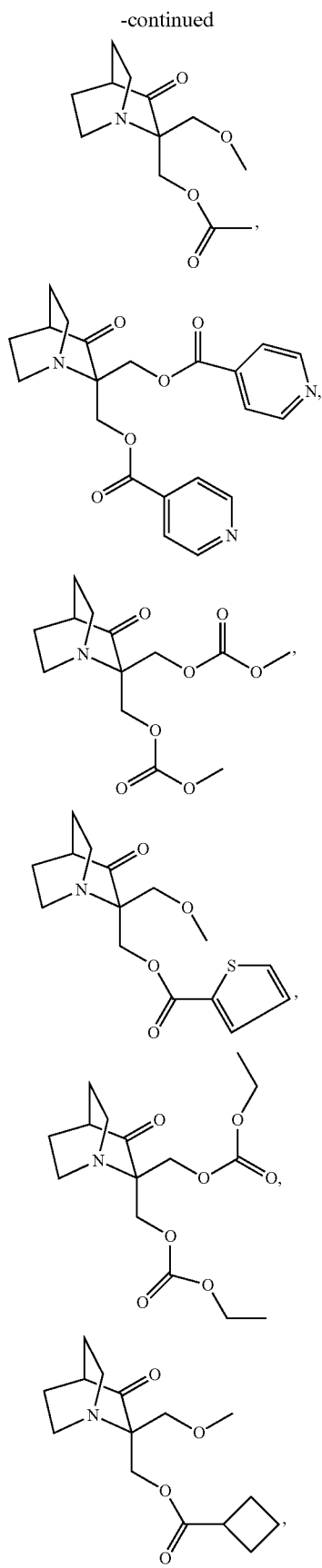
-continued
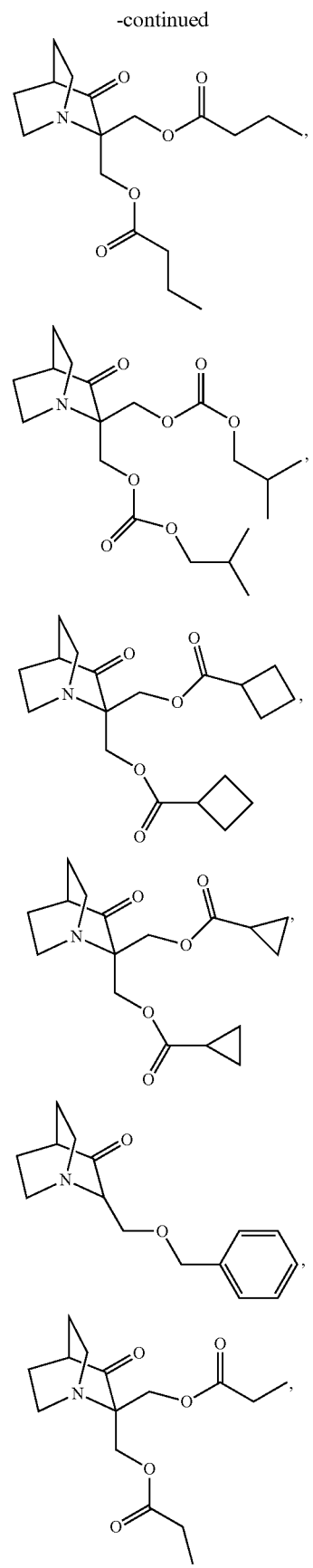

-continued
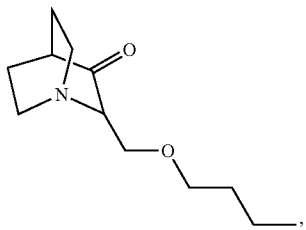
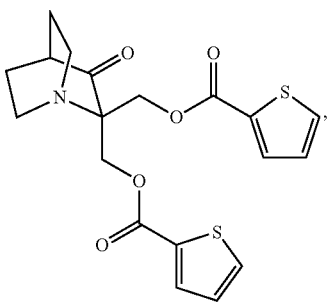
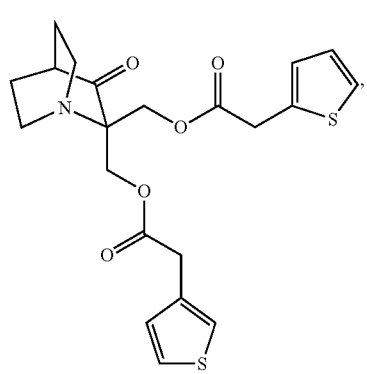
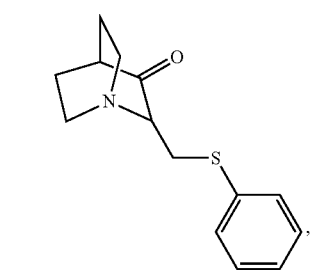
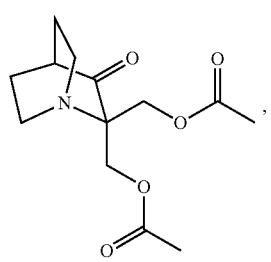
-continued
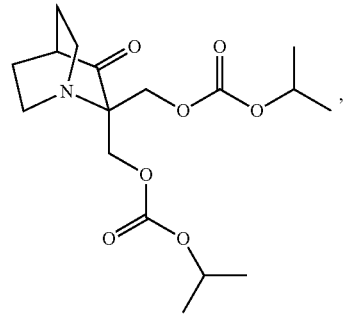
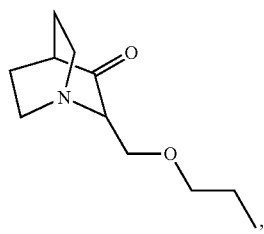
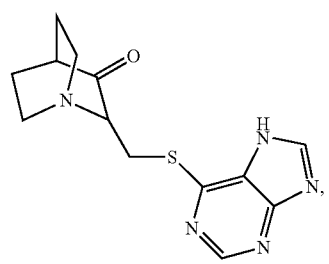
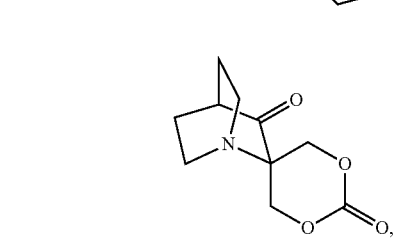
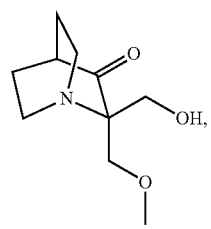
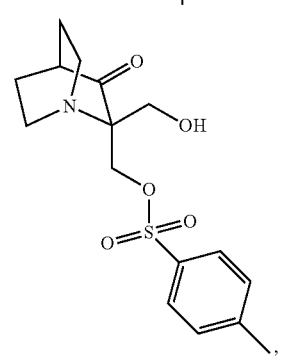

-continued
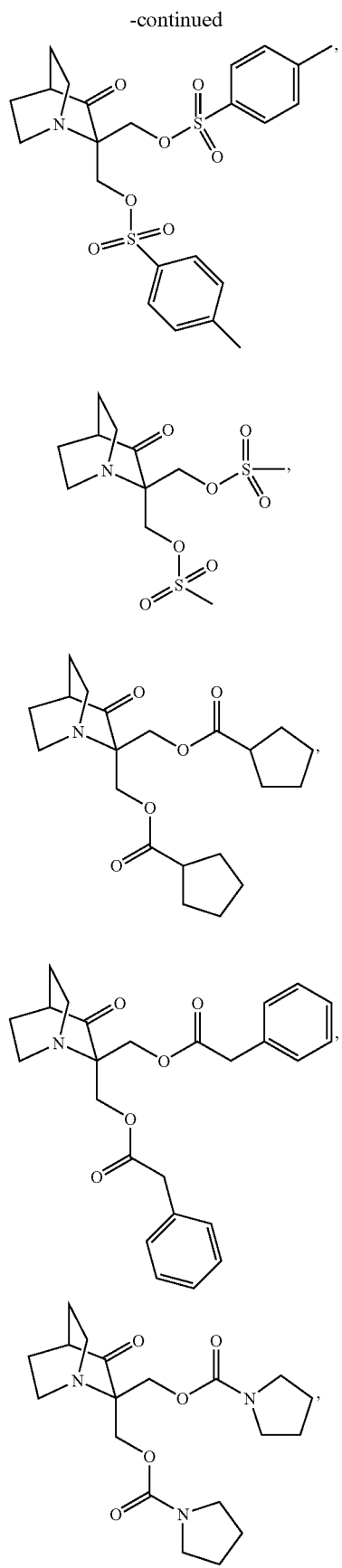
13. A compound selected from the group consisting of:
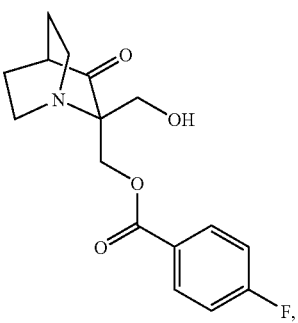

51
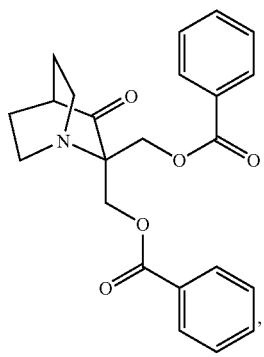
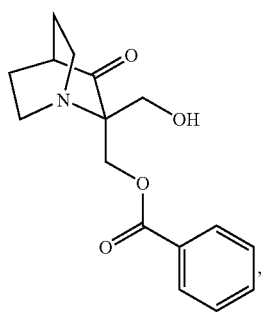
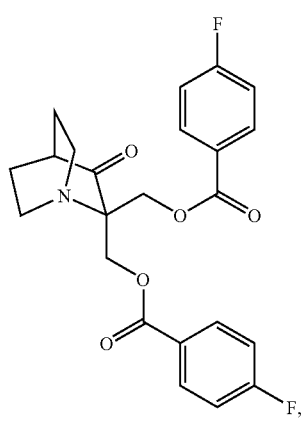
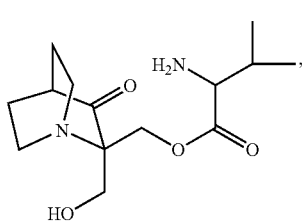
52
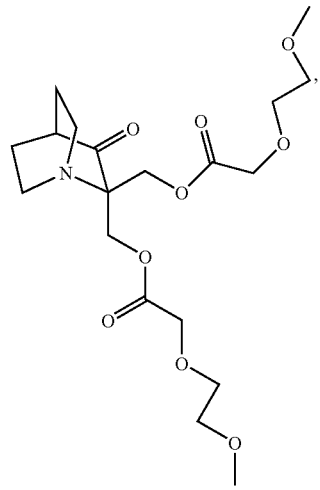
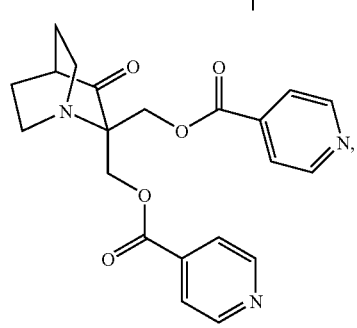
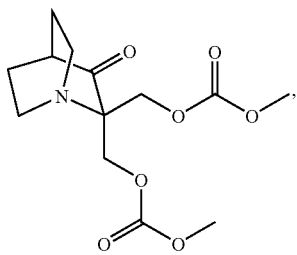
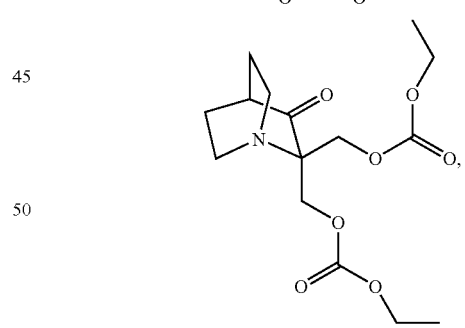
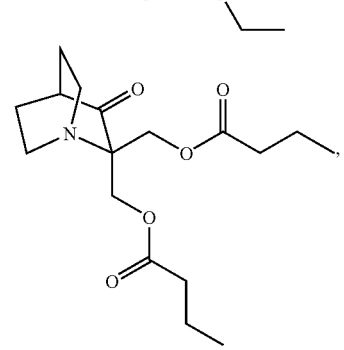

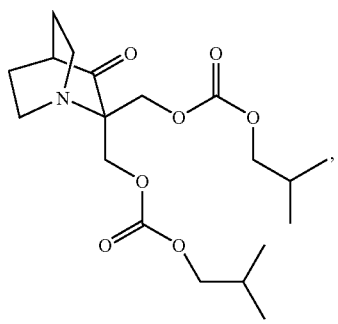
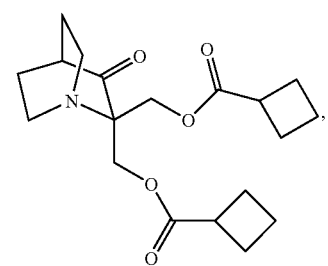
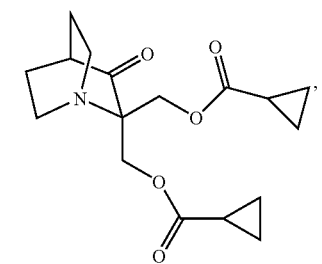
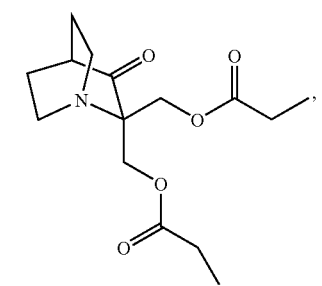
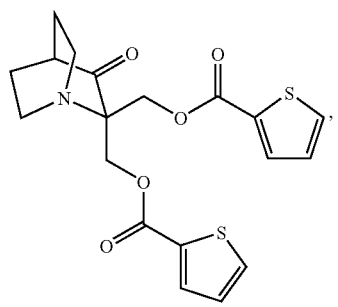
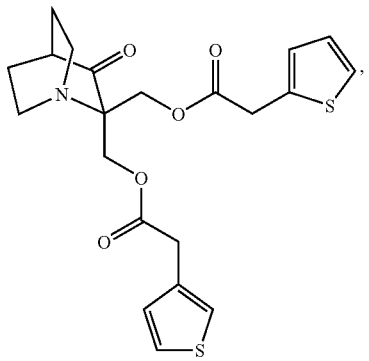
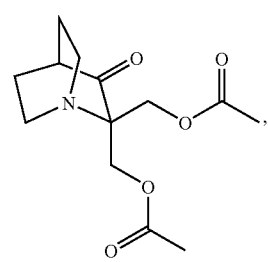
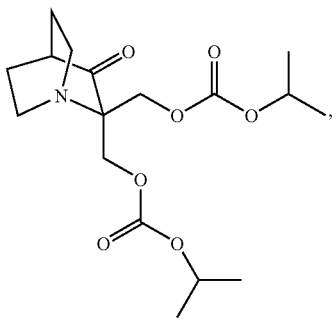
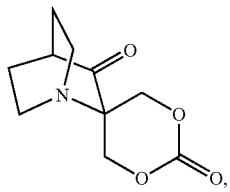
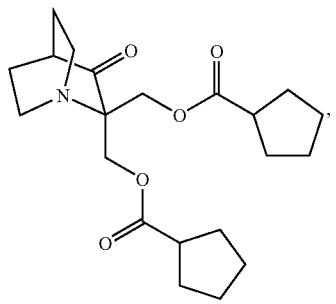

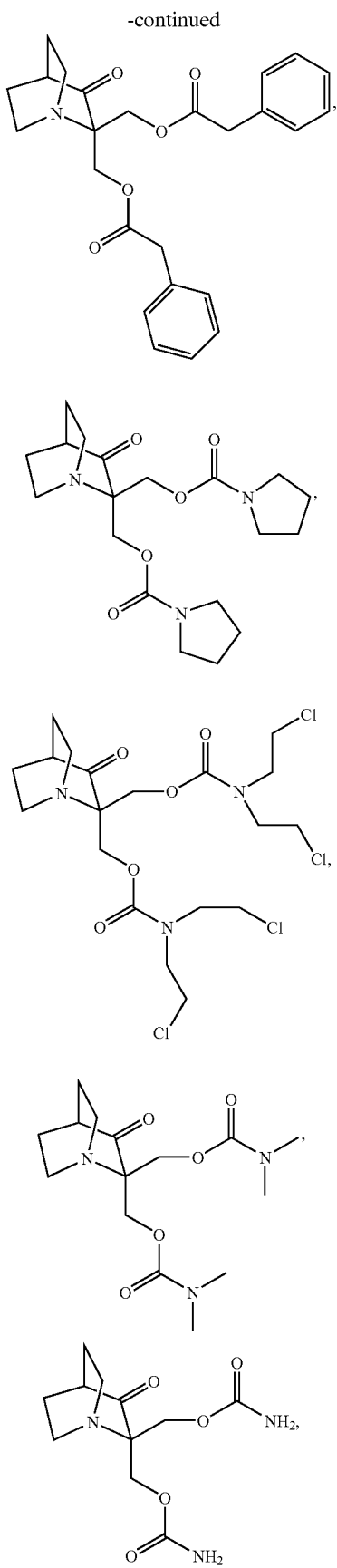

14. The process according to claim 2, wherein X is Cl.

15. A compound of formula (I)

wherein
R¹ and R² are the same or different and are both selected from the group consisting of —CH₂—O—CO—R⁵, CH₂—O—CO—NR⁴R⁵ and —CH₂—O—CO—OR⁵;
R³ is =O;
R⁴ and R⁵ are the same or different and are selected from H; substituted or non-substituted, unbranched or branched, saturated or unsaturated C3-C12 cycloalkyl or C1-C10 alkyl; substituted or non-substituted benzyl; substituted or non-substituted mono- or bicyclic aryl; substituted or non-substituted mono-, bi- or tricyclic C1-C10 heteroaryl or non-aromatic C1-C10 heterocyclyl wherein the heteroatoms are independently selected from N, O and S; or R⁴ and R⁵ in —NR⁴R⁵ are bonded together and form, together with the nitrogen atom to which they are bonded, a substituted or non-substituted non-aromatic C1-C10 mono- or bicyclic heterocyclyl optionally containing one or several further heteroatoms independently selected from N, O and S and optionally comprising one or several cyclic keto groups;

wherein the substituents of the substituted groups are selected from unbranched or branched, saturated or unsaturated C3-C12 cycloalkyl or C1-C10 alkyl; halogen; mono- or bicyclic aryl; mono-, bi- or tricyclic C1-C10 a heteroaryl or non-aromatic C1-C10 heterocyclyl wherein the heteroatoms are independently selected from N, O and S; C1-C10 alkyloxy; amino; C1-C10 alkylamino; $COR^6$; $CONR^6R^7$; and $COOR^6$;

$R^6$ and $R^7$ are the same or different and are selected from H; unbranched or branched, saturated or unsaturated C3-C12 cycloalkyl or C1-C10 a alkyl; benzyl; mono- or bicyclic aryl; mono-, bi- or tricyclic heteroaryl or non-aromatic C1-C10 heterocyclyl wherein the hetero-atoms are independently selected from N, O and S; or a pharmaceutically acceptable salt thereof.

16. A compound according to claim 13, or a pharmaceutically acceptable salt thereof, for use as a medicament.

17. A compound according to claim 15, or a pharmaceutically acceptable salt thereof, for use as a medicament.

18. A method of treating a cancer comprising administering an effective amount of the compound according to claim 13 to a patient in need thereof.

19. A method of treating a cancer comprising administering an effective amount of the compound according to claim 15 to a patient in need thereof.

20. A pharmaceutical composition comprising a therapeutically effective amount of the compound according to claim 13.

21. A pharmaceutical composition comprising a therapeutically effective amount of the compound according to claim 15.

* * * * *

UNITED STATES PATENT AND TRADEMARK OFFICE
CERTIFICATE OF CORRECTION

PATENT NO. : 7,759,361 B2  Page 1 of 1
APPLICATION NO. : 10/590054
DATED : July 20, 2010
INVENTOR(S) : Westman et al.

It is certified that error appears in the above-identified patent and that said Letters Patent is hereby corrected as shown below:

Column 39, line 15, delete "form an substituted" and insert --form a substituted--.
Column 39, lines 18-19, delete "C1-C10 a alkyl" and insert --C1-C10 alkyl--.
Column 39, line 20, delete "C1-C10 a heteroaryl" and insert --C1-C10 heteroaryl--.
Column 39, lines 20-21, delete "C1-C10 a heterocyclyl" and insert --C1-C10 heterocyclyl--.
Column 39, line 22, delete "C1-C10 a alkyloxy" and insert --C1-C10 alkyloxy--.
Column 39, line 23, delete "C1-C10 a alkylamino" and insert --C1-C10 alkylamino--.
Column 39, line 27, delete "C1-C10 a alkyl" and insert --C1-C10 alkyl--.
Column 40, line 23, delete "are –$CH_2$;" and insert --are –$CH_2OH$--.
Column 40, line 42, delete "A of formula (I)" and insert --A compound of formula (I)--.
Column 41, line 17, delete "$CONR^5R^7$" and insert --$CONR^6R^7$--.
Column 42, line 3, delete "$COR^5$" and insert --$COR^6$--.
Column 56, line 51, delete "$CH_2$-O-CO-$NR^4R^5$" and insert -- -$CH_2$-O-CO-$NR^4R^5$--.
Column 57, line 5, delete "C1-C10 a heteroaryl" and insert --C1-C10 heteroaryl--.
Column 57, line 11, delete "C1-C10 a alkyl" and insert --C1-C10 alkyl--.

Signed and Sealed this
Twenty-eighth Day of December, 2010

David J. Kappos
*Director of the United States Patent and Trademark Office*